United States Patent [19]

Koga et al.

[11] Patent Number: 5,849,956

[45] Date of Patent: Dec. 15, 1998

[54] ANTIFUNGAL TERPENE COMPOUNDS AND PROCESS FOR PRODUCING THE SAME

[75] Inventors: Jinichiro Koga; Toyozo Yamauchi; Masaru Shimura; Yoko Ogasawara, all of Niigata; Nagakatsu Ogasawara, Tokyo; Jyunko Suzuki, Niigata, all of Japan

[73] Assignee: Plant Biological Defense System Laboratories, Niigata, Japan

[21] Appl. No.: 875,760

[22] PCT Filed: Feb. 7, 1996

[86] PCT No.: PCT/JP96/00259

§ 371 Date: Aug. 8, 1997

§ 102(e) Date: Aug. 8, 1997

[87] PCT Pub. No.: WO96/24681

PCT Pub. Date: Aug. 15, 1996

[30] Foreign Application Priority Data

Feb. 8, 1995 [JP] Japan .................................. 7-043520
Mar. 20, 1995 [JP] Japan .................................. 7-087396
Jun. 27, 1995 [JP] Japan .................................. 7-183498

[51] Int. Cl.$^6$ .................................. C07C 49/307
[52] U.S. Cl. .......................... 568/326; 568/338; 514/691; 514/729
[58] Field of Search .................................. 568/326, 338; 414/691, 729

[56] References Cited

FOREIGN PATENT DOCUMENTS 1-218591  8/1989  Japan .
4-197186  7/1992  Japan .

OTHER PUBLICATIONS

Koga et al, Tetrahedron, vol. 51, #29, pp. 7907–7918, 1995.
Bohlmann et al; Phytochemistry, vol. 22, #07, pp. 1645–1651, 1983.
Koga et al, Phytochemistry, vol. 44, #02, pp. 249–253, 1997.
D. Cartwright et al, "Chemical Activation of Host Defence Mechanisms as a Basis for Crop Protection", Nature, vol. 267, Jun. 9, 1977, pp. 511–513.
T. Akatsuka et al, "3–Hydroxy–7–oxo–sandaracopimaradiene (Oryzalexin A), a New Phytoalexin Isolated from Rice Blast Leaves", Agric. Biol. Chem., vol. 47, No. 2, 1983, pp. 445–447.
Y. Kono et al, "Absolute Configuration of Oryzalexin A and Structures of Its Related Phytoalexins Isolated from Rice Blast Leaves Infected with *Pyricularia oryzae*", Agric. Biol. Chem., vol. 48, No. 1, 1984, pp. 253–255.
T. Akatsuka et al, "Novel Phytoalexins (Oryzalexins A,B and C) Isolated from Rice Blast Leaves Infected with *Pyricularia oryzae*. Part 1: Isolation, Characterization and Biological Activities of Oryzalexins", Agric. Biol. Chem., vol. 49, No. 6, 1985, pp. 1689–1694.

Y. Kono et al, "Novel Phytoalexins (Oryzalexins A, B and C) Isolated from Rice Blast Leaves Infected with *Pyricularia oryzae*. Part ll: Structural Studies of Oryzalexins", Agric. Biol. Chem., vol. 49, No. 6, 1985, 1695–1701.
H. Sekido et al, "Oryzalexin D (3,7–Dihydroxy–(+)–sandaracopimaradiene), a New Phytoalexin Isolated from Blas–infected Rice Leaves", J. Pesticide Sci., vol. 11, 1986, pp. 369–372.
H. Kato et al, "Oryzalexin E, A Diterpene Phytoalexin from UV–Irradiated Rice Leaves", Phytochemistry, vol. 33, No. 1, 1993, pp. 79–81.
H. Kato et al, "Oryzalexin F, A Diterpene Phytoalexin from UV–Irradiated Rice Leaves", Phytochemistry, vol. 36, No. 2, 1994, pp. 299–301.
O. Kodama et al, "Oryzalexin S, a Novel Stemarane–type Diterpene Rice Phytoalexin", Biosci. Biotech. Biochem., vol. 56, No. 6, 1992, pp. 1002–1003.
O. Kodama et al, "Sakuranetin, a Flavanone Phytoalexin from Ultraviolet–Irradiated Rice Leaves", Phytochemistry, vol. 31, No. 11, 1992, pp. 3807–3809.
M. Watanabe et al, "Novel $C_{19}$–Kaurane Type of Diterpene (Oryzalide A), a New Antimicrobial Compound Isolated from Healthy Leaves of a Bacterial Leaf Blight–resistant Cultivar of Rice Plant", Agric. Biol. Chem., vol. 54, No. 4, 1990, pp. 1103–1105.
Y. Kono et al, "Structures of Oryzalides A and B, and Oryzalic Acid A, A Group of Novel Antimicrobial Diterpenes, Isolated from Healthy Leaves of a Bacterial Leaf Blight–resistant Cultivar of Rice Plant", Agric. Biol. Chem., vol. 55, No. 3, 1991, pp. 803–811.
M. Watanabe et al, "Structures of Oryzalic Acid B and Three Related Compounds, a Group of Novel Antibacterial Diterpenes, Isolated from Leaves of a Bacterial Leaf Blight–Resistant Cultivar of Rice", Biosci. Biotech. Biochem., vol. 56, No. 1, 1992, pp. 113–117.
F. Bohlmann et al, "Diterpenes and Sesquiterpenes from Osteospermum Species", Phytochemistry, vol. 22, No. 7, 1983, pp. 1645–1651.

*Primary Examiner*—Paul J. Killos
*Assistant Examiner*—Sreeni Padmanabhan
*Attorney, Agent, or Firm*—Oblon, Spivak, McClelland, Maier & Neustadt, P.C.

[57] ABSTRACT

The present invention relates to phytocassanes which are novel diterpene compounds exhibiting an antifungal activity against rice blast fungus, *Pyricularia oryzae* (*Magnaporthe grisea*) and rice sheath blight fungus, *Rhizoctonia solani*, and more specifically, it relates to phytocassanes A, B, C, D, and EL and a process for producing phytocassanes or momilactones, antifungal diterpene compounds, at a high yield.

10 Claims, 26 Drawing Sheets

ANTIFUNGAL TERPENE COMPOUNDS AND PROCESS FOR PRODUCING THE SAME

This is the U. S. National Stage Application of PCT/JP96/00259 filed Feb. 7, 1996 now WO96/24681 published Aug. 15, 1996.

TECHNICAL FIELD

The present invention relates to phytocassanes which are rice phytoalexins and are novel diterpene compounds exhibiting an antifungal activity against rice blast fungus, *Pyricularia oryzae* (*Magnaporthe grisea*) and rice sheath blight fungus, *Rhizoctonia solani*, and more specifically, it relates to phytocassanes A, B, C and D. Phytocassanes A, B, C and D according to the present invention have a high antifungal activity against *Pyricularia oryzae* and *Rhizoctonia solani* and are useful for protecting rice plants from rice blast and rice sheath blight.

In addition, the present invention relates a process for producing phytocassanes or momilactones, antifungal diterpene compounds, at a high yield comprising adding cellular extracts of plant pathogenic fungi such as *Pyricularia oryzae* or potato pathogenic fungi to the liquid culture medium of rice calluses to yield phytocassanes and momilactones, diterpene compounds exhibiting an antifungal activity against Pyricularia oryzae and so forth and then separating the product.

Further, the present invention relates to phytocassane EL, a novel diterpene compound having an activity of deriving phytoalexins extracted from rice plants; more specifically, it relates to phytocassane EL having an activity of deriving the formation of phytoalexins in rice plants and exhibiting an antifungal activity against *Pyricularia oryzae* and *Rhizoctonia solani* itself, and a process for producing the same, and low-toxic and harmless rice disease control drugs free from so-called residual toxicity. Since phytoalexins have a high antifungal activity against these pathogenic fungi, they can prevent rice plants from being infected with *Pyricularia oryzae* and *Rhizoctonia solani* by applying phytocassane EL according to the present invention onto rice plants.

TECHNICAL BACKGROUND

Plants perform self-defense against various kinds of stress causing diseases such as the invasion of pathogenic fungi, actions by ultraviolet rays and heavy metals and injuries, according to various kinds of resistance mechanism. As physiologically active substances concerned in such a disease resistance reaction of plants can be mentioned antifungal substances and plant hormones. Of them, the former inhibits the growth of pathogenic fungi directly, while the latter is concerned in the expression of symptoms of a disease.

As antifungal substances of plants, various types have been reported; they are generally classified into four groups according to the expression mechanism, namely, prohibiting, inhibiting, post inhibitins and phytoalexins. Of them, prohibitins are antifungal substances being present at a sufficient concentration on a sound plant tissue; inhibitins are antifungal substances being present at a low concentration on a sound plant tissue and the concentration thereof increases after they are infected with pathogenic fungi, and post inhibitins are substances being present on a sound plant tissue and exhibiting an antifungal activity according to a simple chemical change thereof when they are invaded with pathogenic fungi though they exhibit no antifungal activity as they are. These three substances are considered to be pre-antifungal substances. In contrast, phytoalexins are antifungal substances being absent on a sound plant tissue and being derived and synthesized after they are infected with pathogenic fungi, and being dynamic defense substances playing an important role in a plant disease resistance reaction.

It is known that plants show an antibiotic reaction (hypersensitive reaction) when they come into contact with pathogenic fungi and yield phytoalexins having an antifungal activity against the pathogenic fungi on a tissue surrounding the reaction site. The antifungal activity of these phytoalexins itself is not so high, but it is thought that they exhibit an antifugnal activity when they are transferred to a disease part and are present at a high concentration locally. Besides, phytoalexins are decomposed rapidly by a sound plant tissue (S. Shibata: Biologically Active Natural Substances, new edition, pp. 66–72, Ishiyaku Shuppan, 1988; M. Nishimura and S. Ouchi: Plant Infection Physiology, pp. 99–121, Bun-eido Shuppan, 1990).

Thus, phytoalexins are natural substances derived from plants yielded by plants themselves, and besides, since they have properties of being decomposed by a sound plant tissue easily and scarcely remain, they have been expected keenly to be utilized as so-called low-toxic and harmless agricultural chemicals from the viewpoint of environmental preservation, and the development of phytoalexins having excellent characteristics of a higher antifungal activity has been desired keenly.

The results of various studies have been reported about a rice phytoalexin of phytoalexins, and the following can be exemplified:

1) Momilactones A and B (formation of momilactones of a rice phytoalexin)
   D. Cartwright, P. Langcake, R. J. Pryce, D. P. Leworthy and J. P. Ride: Nature, 267, 511–513 (1977)
2) Oryzalexin A (Isolation of oryzalexin A of a novel phytoalexin from blast-infected rice leaves)
   T. Akatsuka, O. Kodama, H. Kato, Y. Kono and S. Takeuchi: Agric. Biol. Chem., 47, 445–447 (1983)
3) Oryzalexins A, B and C (Report on Chemical Structures, short report)
   Y. Kono, S. Takeuchi, O. Kodama and T. Akatsuka: Agric. Biol. Chem., 48, 253–255 (1984)
4) Oryzalexins A, B and C (Isolation of oryzalexins A, B and C, properties, antifungal activity against *Pyricularia oryzae*)
   p1 T. Akatsuka, O. Kodama, H. Sekido, Y. Kono and S. Takeuchi: Agric. Biol. Chem., 49, 1689–1694 (1985)
5) Oryzalexins A, B and C (Detailed Report on Structures)
   Y. Kono, S. Takeuchi, 0. Kodama, H. Sekido and T. Akatsuka: Agric. Biol. Chem., 49, 1695–1701 (1985)
6) Oryzalexin D (Isolation, structure, activity)
   H. Sekido, T. Endo, R. Suga, O. Kodama, T. Akatsuka, Y. Kono and S. Takeuchi: J. Pesticide Sci., 11, 369–372 (1986)
7) Oryzalexin E (Isolation of oryzalexin E of a novel rice phytoalexin from ultraviolet-irradiated rice plants, structure, activity of it)
   H. Kato, O. Kodama and T. Akatsuka: Phytochemistry, 33, 79–81 (1993)
8) Oryzalexin F (Isolation of oryzalexin F of a novel rice phytoalexin from ultraviolet-irradiated rice plants, structure, activity of it)
   H. Kato, O. Kodama and T. Akatsuka: Phytochemistry, 36, 299–301 (1994)
9) Oryzalexin S (Isolation of oryzalexin S of a novel rice phytoalexin from ultraviolet-irradiated rice plants, structure of it)

O. Kodama, W. X. Li, S. Tamogami and T. Akatsuka: Biosci. Biotech. Biochem., 56, 1002–1003 (1992)

10) Sakuranetin (Isolation of flavanone-skeleton phytoalexins from ultraviolet-irradiated rice plants and activity against Pyricularia oryzae)

O. Kodama, J. Miyakawa, T. Akatsuka and S. Kiyosawa: Phytochemistry, 31, 3807–3809 (1992)

11) Oryzaride A (Isolation of oryzaride A having an antifungal activity against *Xanthomonas oryzae* from bacterial leaf blight of rice plants, short report)

M. Watanabe, Y. Sakai, T. Teraoka, H. Abe, Y. Kono, J. Uzawa, K. Kobayashi, Y. Suzuki and A. Sakurai: Agric. Biol. Chem., 54, 1103–1105 (1990)

12) Oryzarides A and B, oryzaric acid A (Isolation of oryzarides A and B, and oryzaric acid A having an antifungal activity against Xanthomonas oryzae from bacterial leaf blight of rice plants)

Y. Kono, J. Uzawa, K. Kobayashi, Y. Suzuki, M. Uramoto, A. Sakiurai, M. Watanabe, T. Teraoka, D. Hosokawa, M. Watanabe and H. Kondo: Agric. Biol. Chem., 55, 803–811 (1991)

13) Oryzaric acid B (Structures of oryzaric acid B and substances A, B and C concerned)

M. Watanabe, Y. Kono, M. Watanabe, J. Uzawa, T. Teraoka, D. Hosokawa, Y. Suzuki, A. Sakurai and M. Teraguchi: Biosci. Biotech. Biochem., 56, 113–117 (1992)

14) Diterpene compounds of osteospermum plants (They are compounds having the same cassane skeleton as a phytocassane though they are not phytoalexins. However, they have different from phytocassanes in the structure, and there is no description about physiological activity.)

Ferdinand Bohlmann, Michael Wallmyer, Jasmin Jakupovic and Jurgen Ziesche: Phytochemistry, 22 (7), 1645–1651 (1983)

Thus, as rice phytoalexins have been known momilactones A and B, oryzalexins A, B, C, D, E, F and S, sakuranetin, oryzalic acids A and B, and oryzarides A and B; however, none having the structure of the general formula (I) has been known yet. No diterpene compound having the structure of (1) has been reported, either.

These phytoalexins are isolated from rice plants, but regarding momilactones A and B, and oryzalexins A, B, C and D, a process for isolating them from liquid cultured cells of rice has been investigated (official gazette of Japanese Laid-Open Patent Publication No. 1-218591). However, said process comprises inoculating Pyricularia oryzae to rice plants directly, employing no cellular extracts of Pyricularia oryzae or potato pathogenic fungi, and the effectiveness of said cellular extracts has not been investigated at all; in addition, the yield thereof is extremely small and practical use thereof has never been expected. Phytocassanes are novel compounds found by the present inventors; phytocassanes A, B, C and D can be collected from resistant reaction sites of rice plants infected with Pyricularia oryzae or Rhizoctonia solani, but no example including a process for the production thereof has never been reported. In addition, according to the studies by the inventors, it has been necessary to cultivate a large amount of rice plants, inoculate pathogenic fungi thereto, collect resistant reaction sites and separate active ingredients in order to utilize phytocassanes as plant disease control drugs.

However, such a process required much labor for the cultivation of plants and the procedure of inoculating pathogenic fungi and had a problem that isolation between plant ingredients and active substances was complicated.

Moreover, a substance yielding and deriving a phytoalexin in a plant is called an elicitor (Keen, N. T.: Science 187, 74–75 (1975), and a lot of such substances have been isolated from plant pathogenic fungi. Typical elicitors include hepta-beta-D-glucopilanoside isolated from Phytophthora megasperma f. sp. glycinea (Sharp, J. K., B. Valentand, P. Albershim: J. Biol. Chem. 259, 11321–11336 (1984)) as a polysuccharide substance, monicolin A isolated from Monilinia fructicola (Cruickshank, I. A. M. and D. R. Perrin: Life Sci. 7, 449–458 (1968)) as a protein substance and eicosapentaenoic acid isolated from Phytophthora infestans (Bostock, R. M., J. Kuc and R. A. Laine: Science 212, 67–69 (1981)) as a lipid.

In addition to elicitors derived from pathogenic fungi, some kinds of agricultural chemicals, antibiotics and heavy metals are known to have an elicitor activity, however, it has never been known that a rice ingredient like phytocassane EL has an elicitor activity.

Since the elicitor derives the production of a phytoalexin having an antifungal activity against pathogenic fungi in a plant, as described above, it is expected that it may be a plant disease control drug with high safety due to an action different from that of conventional synthetic agricultural chemicals; however, there have been reported only few examples of practical use thereof actually, and hence, the development of a plant disease control drug with high safety utilizing such a substance producing and deriving a phytoalexin has been desired keenly in the field concerned.

DISCLOSURE OF THE INVENTION

Under these circumstances, the present inventors have engaged in assiduous studies about new phytoalexin substances produced by a plant resistant reaction, and as a result have found novel dipertene compounds never reported before and at the same time have found that said novel compounds have a high antifungal activity against rice blast fungus, *Pyricularia oryzae* and rice sheath blight fungus, *Rhizoctonia solani*. That is, the present inventors have found that substances having an antifungal activity against *Pyricularia oryzae* and *Rhizoctonia solani* are produced at plant sites (leaves and stems) where rice plants infected with *Pyricularia oryzae* or *Rhizoctonia solani* show a resistant reaction (hypersensitive reaction), and besides they have succeeded in isolating the active substances according to a means such as extraction with a solvent and column chromatography. And they have made it clear that these antifungal substances are phytocassanes of novel substances having the following general formula (I) and that these substances are useful as active ingredients of *Pyricularia oryzae* control drugs and Rhizoctonia solani control drugs.

It is an object of the present invention to provide phytocassanes A, B, C and D of novel dipertene compounds which are rice phytoalexins and have an antifungal activity against *Pyricularia oryzae* and *Rhizoctonia solani*.

It is another object of the present invention to provide novel substances having a high antifungal activity against *Pyricularia oryzae* and being useful as active ingredients of *Pyricularia oryzae* control drugs.

It is another object of the present invention to provide novel substances having a high antifungal activity against *Rhizoctonia solani* and being useful as active ingredients of *Rhizoctonia solani* control drugs.

Moreover, the present inventors have taken note of a process for culturing a liquid of plant calluses often employed for the production of plant components and have tested a process for culture by adding cellular extracts of plant pathogenic fungi such as *Pyricularia oryzae* and potato pathogenic fungi into a culture broth of rice calluses as phytocassane and momilactone derivative substances, and as a result have found that large amounts of phytocassanes or momilactones can be obtained easily at a high yield over a short period of time by employing cellular extracts of plant pathogenic fungi such as *Pyricularia oryzae* and potato pathogenic fungi.

It is still another object of the present invention to provide a process for producing phytocassanes comprising adding cellular extracts of plant pathogenic fungi such as *Pyricularia oryzae* and potato pathogenic fungi into a culture broth of rice calluses as phytocassane derivative substances to produce phytocassanes and isolating them.

It is still another object of the present invention to provide a process for producing momilactones comprising adding cellular extracts of plant pathogenic fungi such as *Pyricularia oryzae* and potato pathogenic fungi into a culture broth of rice calluses as momilactone derivative substances to produce momilactones and isolating them.

Further, the present inventors have engaged in assiduous studies about substances producing and deriving phytoalexines in rice plants, and as a result have found that one of rice ingredients has such an activity. Besides, they have found that the substance has an antifungal activity against pathogenic fungi and can be produced efficiently by a culture broth of rice calluses. Moreover, they have isolated the substance according to a means such as extraction with a solvent and column chromatography and have performed the structural analysis thereof, and as a result they have revealed that the substance is phytocassane EL, a novel substance having the following structure, and is effective as a *Pyricularia oryzae* and *Rhizoctonia solani* control drug.

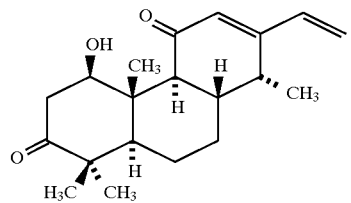

It is still another object of the present invention to provide phytocassane EL, which is an elicitor deriving the formation of phytoalexines in rice plants and is a novel substance having an antifungal activity against *Pyricularia oryzae* and *Rhizoctonia solani*.

It is still another object of the present invention to provide a process for producing phytocassane EL by collecting phytocassane EL from a culture broth of rice calluses.

It is still another object of the present invention to provide *Pyricularia oryzae* and *Rhizoctonia solani* control drugs capable of preventing damage due to *Pyricularia oryzae* and damage due to *Rhizoctonia solani* by applying phytocassane EL onto rice plants.

A first embodiment of the present invention dissolving the above problems relates to dipertene compounds of phytocassanes A, B, C and D represented by the following general formula (I), (wherein $R_1$, $R_2$ and $R_3$ represent the following substituents respectively), which are rice phytoalexins and have an antifungal activity against *Pyricularia oryzae* and *Rhizoctonia solani*.

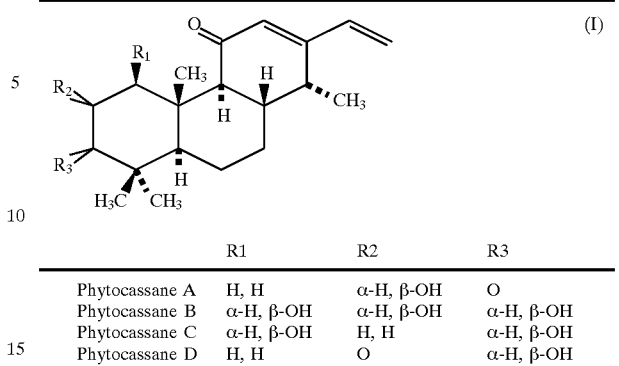

|  | R1 | R2 | R3 |
|---|---|---|---|
| Phytocassane A | H, H | α-H, β-OH | O |
| Phytocassane B | α-H, β-OH | α-H, β-OH | α-H, β-OH |
| Phytocassane C | α-H, β-OH | H, H | α-H, β-OH |
| Phytocassane D | H, H | O | α-H, β-OH |

As described above, phytocassanes A, B, C and D according to the present invention are plant-derived substances produced on plant sites (leaves and stems) where rice plants infected with *Pyricularia oryzae* or *Rhizoctonia solani* show a resistant reaction (hypersensitive reaction), and such active substances can be isolated as single ingredients by collecting proper sites of leaves and stems of such rice plants, subjecting them as starting materials to an extraction treatment with a solvent such as ethyl acetate, methanol, ethanol and acetone and purifying the resultant product according to a means such as high-performance liquid chromatography and thin-layer chromatography.

As a specific process for purification can be mentioned a process comprising extracting the starting materials with a solvent, adsorbing the resultant product according to column chromatography on a Sep Pack C-18 column, eluting phytocassane fractions to isolate them, and purifying and isolating them according to a process for purification including fractionation of them by high performance liquid chromatography (HPLC) on a column such as TSKgel ODS-120, concentration of them and the like; however, it is possible, in addition to said process, to perform purification by combining other similar means of purification properly, and the process for purification is not particularly restricted.

Phytocassanes A, B, C and D of the present invention are novel substances and have the following properties.

1) Phytocassanes A, B, C and D are all colorless gum-like substances and are soluble in acetone, chloroform, methanol and ethanol; they are dissolved in water containing a surface active agent at a concentration of about 100 ppm.

2) The high precision molecular weights thereof according to high resolution mass spectrometer analysis are as below:

Phytocassane A: 316.2052 (calculated value as $C_{20}H_{28}O_3$: 316.2065)

Phytocassane B (as with one hydrogen atom added: 335.2286 (calculated value as $C_{20}H_{31}O_4$: 335.2223)

Phytocassane C: 318.2164 (calculated value as $C_{20}H_{30}O_3$: 318.2133)

Phytocassane D: 316.2048 (calculated value as $C_{20}H_{28}O_3$: 316.2065)

3) Phytocassanes A, B, C and D show infrared absorption spectra shown in FIGS. 1–4.

4) Phytocassanes A, B, C and D show $^1$H-NMR spectra shown in FIGS. 5–8.

5) Phytocassanes A, B, C and D show $^{13}$C-NMR spectra shown in FIGS. 9–12.

6) Phytocassanes A, B, C and D show CD spectra (circular dichroism) shown in FIGS. 13–16.

7) Phytocassanes A, B, C and D have properties of inhibiting spore germination of *Pyricularia oryzae* and can inhibit the outbreak of blast when they are applied onto rice plants. The concentration of a phytocassane inhibiting spore germination of Pyricularia oryzae by 50% is 10 ppm in phytocassane A, 3 ppm in phytocassane B, 6 ppm in phytocassane C and 20 ppm in phytocassane D.

8) Phytocassanes A, B, C and D have properties of inhibiting hypha extension of *Rhizoctonia solani* and can inhibit the outbreak of rice sheath blight when they are applied onto rice plants. Regarding the concentration of a phytocassane inhibiting hypha extension of *Rhizoctonia solani*, hypha extension is inhibited at 17 ppm considerably in phytocassane A, at 15 ppm perfectly in phytocassane B, and at 10 ppm perfectly in phytocassane C. Hypha extension is inhibited at 50 ppm considerably in phytocassane D.

As is apparent from the results of a test for inhibitory effects on the rice blast fungus and a test for inhibitory effects on hypha extension of rice sheath blight fungus shown in Examples to be described later, phytocassanes A, B, C and D have properties of inhibiting spore germination and hypha extension of *Pyricularia oryzae* and hypha extension of *Rhizoctonia solani* and are useful as active ingredients of Pyricularia oryzae control drugs and Rhizoctonia solani control drugs. Since phytocassanes A, B, C and D of the present invention have the above-described various properties, the outbreak of blast and the outbreak of rice sheath blight can be controlled by applying said compounds onto rice plants as an agent with a proper form. The form of drugs for applying said compounds onto rice plants, the form for use thereof and a method of administration are not particularly restricted; for example, drugs comprising said compounds as active ingredients with a proper molecular weight and a proper form are prepared according to the above concentrations inhibiting spore germination of *Pyricularia oryzae* by 50% as a standard and administered according to an ordinary procedure.

Phytocassanes A, B, C and D of the present invention are natural substances produced in rice plants and have properties of being decomposed easily by a sound plant tissue with few residues; hence, not only they have a high antifungal activity against *Pyricularia oryzae* and *Rhizoctonia solani*, practicability thereof is extremely significant as a so-called low-toxic and harmless antifungal agent, the development of which has been expected from the viewpoint of environmental preservation.

A second embodiment of the present invention dissolving the above problems relates to a process for producing antifungal terpene compounds comprising adding cellular extracts of plant pathegenic fungi such as *Pyricularia oryzae* or potato pathogenic fungi to the liquid culture medium of rice calluses to produce antifungal terpene compounds and separating them. As the liquid culture medium of rice calluses to be used in the present invention can be employed any of the culture media comprising a carbon source, a nitrogen source, inorganic salts, vitamins and plant hormones which have been used for the tissue culture of rice plants, and the DK culture medium is preferable.

Carbohydrates such as sucrose are used in these culture media as a carbon source, and as inorganic salts and a nitrogen source can be used potassium nitrate, ammonium sulfate, calcium chloride, aspartic acid and glutamine. As vitamins can be used nicotinic acid, hydrochloric acid thiamine and hydrochloric acid pyridoxine. As plant hormones can be used properly 2,4-D, kinetin, abscisic acid and indoleacetic acid.

The kind of rice plants and a tissue site employed are not particularly restricted; a callus prepared from seeds of Koshihikari is preferable. The formation of rice calluses is not particularly restricted but can be performed according to an ordinary procedure; preferably, an albumen and an embryo site of rice seeds from which rice husks are removed may be cultured in a germless condition, in a medium obtained by adding 2,4-D to the above liquid medium in a double amount and removing aspartic acid and glutamine; for example, rice calluses are formed by culturing them under the conditions of a pH of 5.8 and 25° C. at a dark place for 30 days.

In the present invention, antifungal terpene compounds are derived by adding cellular extracts of plant pathogenic fungi such as *Pyricularia oryzae* or potato pathogenic fungi to the liquid culture medium of rice calluses.

A preferable process for producing cellular extract ingredients of plant pathogenic fungi such as Pyricularia oryzae or potato pathogenic fungi which are phytocasane derivative substances can be exemplified as below. Onto a rye liquid culture medium (containing a water extract of 60 g of rye seeds, 20 g of saccharose and 2 g of a yeast extract in 1 L) are inoculated each fungus; Pyricularia oryzae is cultured under shaking at 28° C. for 5 to 7 days, and potato pathogenic fungi are cultured under being left to stand at 18° C. for one month. Each culture broth is filtered isolate the fungus. To about 50 g of fungi are added 180 ml of water; the obtained product is ground by a homogenizer and pulverized by ultrasound, and then heat-decomposed by an autoclave (121° C., 60 minutes). A supernatant obtained by subjecting the decomposed product to centrifugal separation is employed as a phytocassane derivative substance sample. A monilactone derivative substance can be prepared in the same manner. It goes without saying that a process for preparing a cellular extract ingredient is not restricted to the above process and that other processes exhibiting the same effect can be employed similarly.

The above phytocassane and momilactone derivative substances are added to the culture broth of calluses, and after the resultant product is cultured for several days, the supernatant is subjected to centrifugal separation. The supernatant is extracted with a solvent such as acetic acid, and the solvent is distilled to obtain a mixture of a rude phytocassane and a rude momilactone. The amount of each ingredient of phytocassanes A, B, C and D and the amount of each ingredient of momilactones A and B can be confirmed according to high performance liquid chromatography (HPLC), and in addition, each ingredient can be obtained singly by collecting the peak of each corresponding ingredient. The conditions of HPLC for separating phytocassanes are as below:

Column: TSKgel ODS-120T (4.6 mm×300 mm)

Solvent: Acetonitrile (45) : Water (55) (volume ratio)

Flow rate: 1 ml/min

Detector: UV 280 nm

The conditions of HPLC for separating momilactones are as below:

Column: TSKgel ODS-120T (4.6 mm×300 mm)

Solvent: Acetonitrile (45) : Water (55) (volume ratio)

Flow rate: 1 ml/min

Detector: UV 215 nm

Phytocassanes A, B, C and D of the present invention can be isolated as a single ingredient by employing the supernatant of the above culture as a starting material, subjecting it to an extraction treatment with a solvent such as ethyl acetate, methanol, ethanol and acetone in the same manner as above and subjecting the reaction product to a purification treatment according to a means such as column chromatography, high performance liquid chromatography and thin layer chromatography.

On the other hand, momilactones A and B are known as substances collecting the germination of rice seeds and having an antifungal activity against *Pyricularia oryzae*, and the molecular formulas and molecular weights of momilactones A and B are as shown below:

Momilactone A: $C_{20}H_{26}O_3$ 314
Momilactone B: $C_{20}H_{26}O_4$ 330

Momilactones A and B have the following chemical structures:

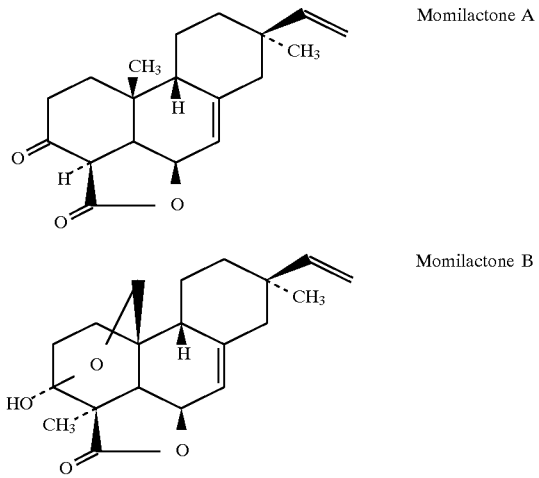

Momilactone A

Momilactone B

Momilactones A and B can be purified in the same manner as in the case of the above phytocassanes, employing the supernatant liquid of the above culture as a starting material.

As will be shown in Examples later, the amounts of momilactones A and B produced were 0.245 µg and 0.864 µg per ml of a culture broth respectively according to a conventional process, but they are 3.3 µg and 10.5 µg according to the present invention; thus, it has been revealed that the yields thereof increase remarkably and that the yields of momilactones can be improved sharply, though it has been difficult to accomplish a high yield thereof.

Moreover, a third embodiment of the present invention dissolving the above problems relates to phytocassane EL having an activity of deriving the formation of a phytoalexin in rice plants and an antifungal activity against *Pyricularia oryzae* and Rhizoctonia solani represented by the following structural formula, a process for producing the above phytocassane EL comprising adding cellular extracts of plant pathogenic fungi such as *Pyricularia oryzae* or potato pathogenic fungi to the liquid culture medium of rice calluses to produce phytocassane EL, and isolating it, and *Pyricularia oryzae* and *Rhizoctonia solani* control agents containing the above phytocassane EL as an active ingredient.

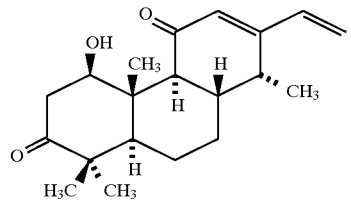

The present inventors have found, in the course of performing various tests measuring the amount of phytoalexins produced in rice plants after a sample is applied onto rice leaves and cultivated properly, that solvent extracts from the liquid culture medium of rice calluses with cellular extracts of plant pathogenic fungi such as *Pyricularia oryzae* or potato pathogenic fungi added thereto have a high activity of deriving phytoalexins. Hence, the active ingredient (phytocassane EL) can be produced, for example, by adding cellular extracts of plant pathogenic fungi such as Pyricularia oryzae or potato pathogenic fungi to the liquid culture medium of rice calluses and culturing it properly, and then, after confirming the formation of phytocassane EL, the culture broth can be isolated as a single ingredient by being subjected to an extraction treatment with a non-water-soluble organic solvent such as ethyl acetate, chloroform and ethyl ether and being purified according to a means such as high performance chromatography and thin layer chromatography.

The above phytocassane EL derivative substance sample is added to the culture broth of calluses, the resultant product is cultured for several days and the supernatant liquid thereof is isolated. As a specific process for purifying phytocassane EL can be exemplified a process comprising subjecting a supernatant to an extraction treatment with ethyl acetate, purifying the extract ingredients according to a purification process such as fractionation by high performance liquid chromatography on TSKgel ODS-120A (manufactured by Toso) or ODS-120T (manufactured by Toso), concentration and the like, and isolating the resultant product as a preferable process; and, in addition to the above process, it is possible to perform purification by combining similar purification means properly and the purification process is not particularly defined.

Phytocassane EL of the present invention is a novel substance and has the following properties:

1) Phytocassane EL is a colorless gum-like substance, is soluble in acetone, chloroform, methanol and ethanol, and is dissolved in water at a concentration of about 100 ppm.

2) The high precise molecular weight of phytocassane EL according to high resolution power mass spectrometer analysis is 16.2062 (calculated value as $C_{20}H_{28}O_3$: 316.2065).

3) Phytocassane EL shows an infrared absorption spectrum shown in FIG. 23.

4) Phytocassane EL shows an $^1$H-NMR spectrum shown in FIG. 24.

5) Phytocassane EL shows a $^{13}$C-NMR spectrum shown in FIG. 25.

6) Phytocassane EL shows a CD (circular dichroism) spectrum shown in FIG. 26.

7) Phytocassane EL has properties of deriving the formation of phytoalexins in rice plants. As derived phytoalexins can be mentioned phytocassanes A, B, C and D and momilactones A and B. Since these substances have a strong antifungal activity against *Pyricularia oryzae* and *Rhizoctonia solani*, rice plants with these substances derived therein are thought to have resistance to fungi.

8) Phytocassane EL has an action of inhibiting spore germination and hypha extension of *Pyricularia oryzae*. The concentration of phytocassane EL inhibiting spore germination by 50% is 7 ppm, and hypha extension is inhibited considerably at this concentration.

9) Phytocassane EL inhibits hypha extension of Rhizoctonia solani at a concentration of 10 ppm.

Phytocassane EL of the present invention has properties of deriving the formation of phytoalexins of antifungal substances in rice plants, inhibiting spore germination and hypha extension of *Pyricularia oryzae* and inhibiting hypha extension of *Rhizoctonia solani*, as will be shown in Examples later, and hence phytocassane EL is useful as an active ingredient of *Pyricularia oryzae* control drugs and *Rhizoctonia solani* control drugs. Since phytocassane EL has various properties as mentioned above, the outbreak of rice blast disease and the outbreak of rice sheath blight can be checked by applying said compound onto rice plants as a drug with a proper form. Drugs according to the present invention may be formed into medicines with a proper form containing the above effective amount thereof according to an object for use, as will be shown in Examples later, and the form and a means of preparing a medicine are not particularly restricted.

As a method of applying said compound onto rice plants can be exemplified preferably a method comprising dissolving said compound into a 20 mM phosphoric acid buffer solution with a pH of 5.5 containing 0.1% Tween 20 and spraying the solution onto rice plants; and, other methods can be employed, and the form of a drug, the way for use and a method of application for applying said compound onto rice plants are not particularly restricted.

BEST EMBODIMENT FOR PERFORMING THE INVENTION

Figure 1:
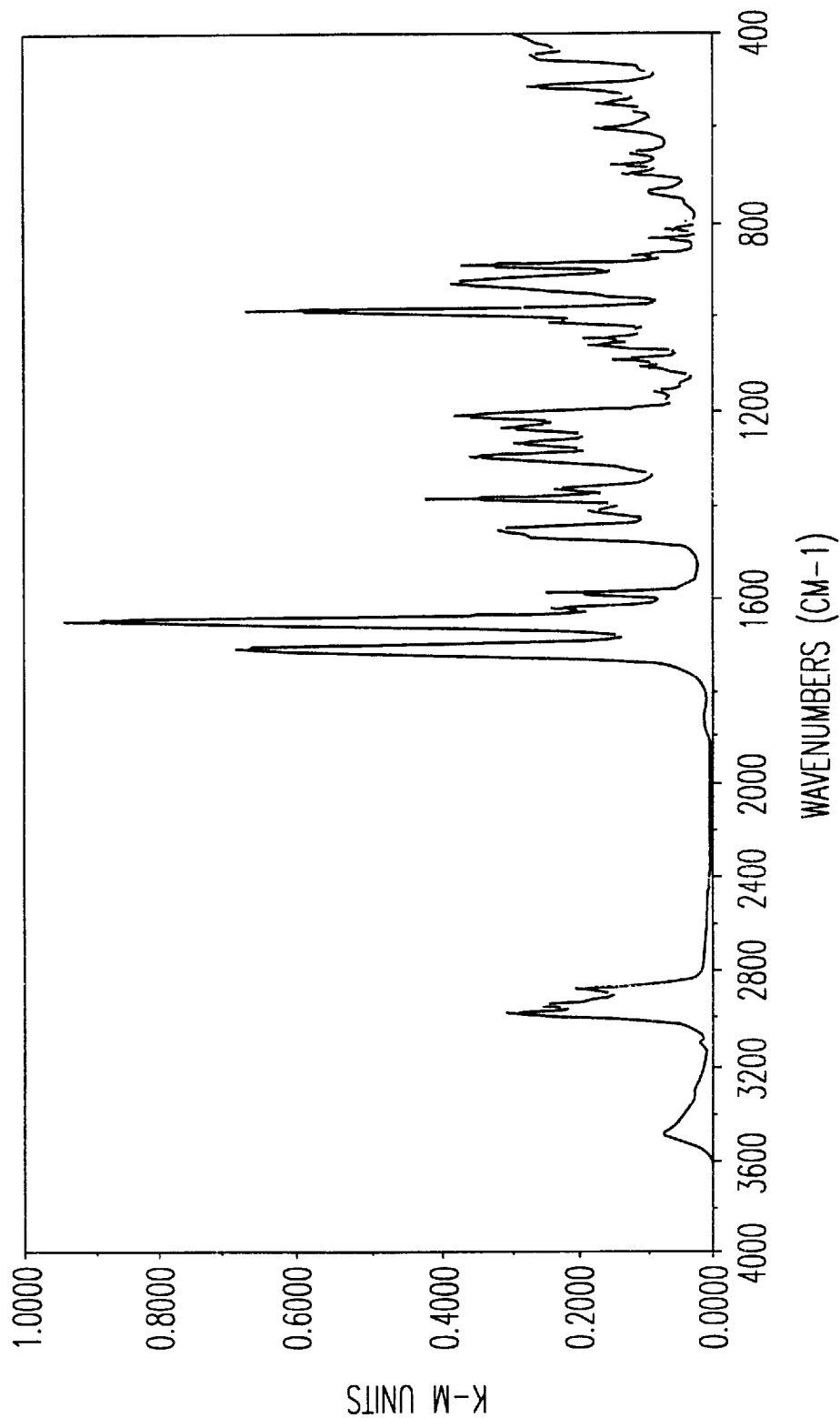
FIG. 1 shows an infrared absorption spectrum of phytocassane A according to the present invention.
Figure 2:
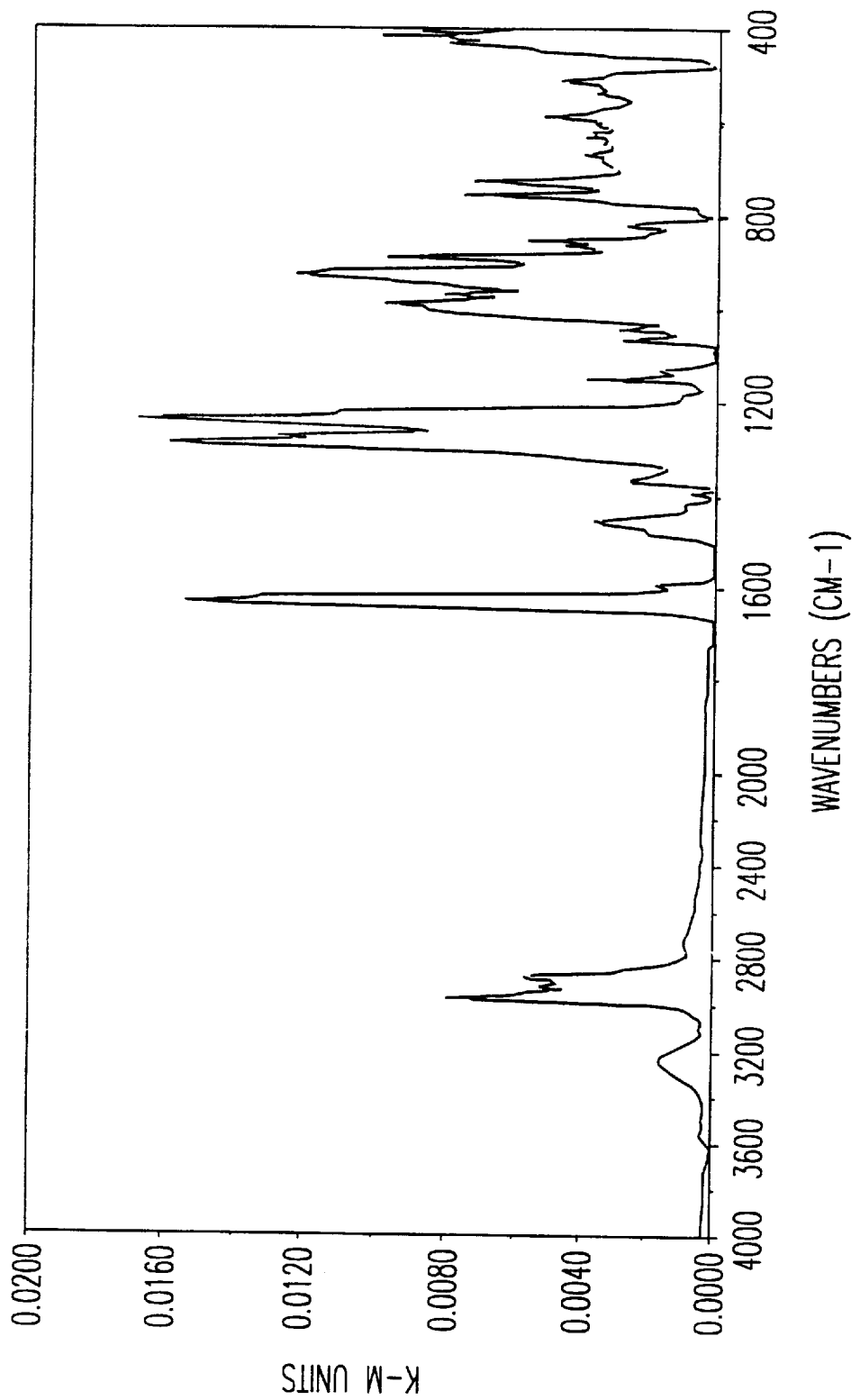
FIG. 2 shows an infrared absorption spectrum of phytocassane B according to the present invention.
Figure 3:
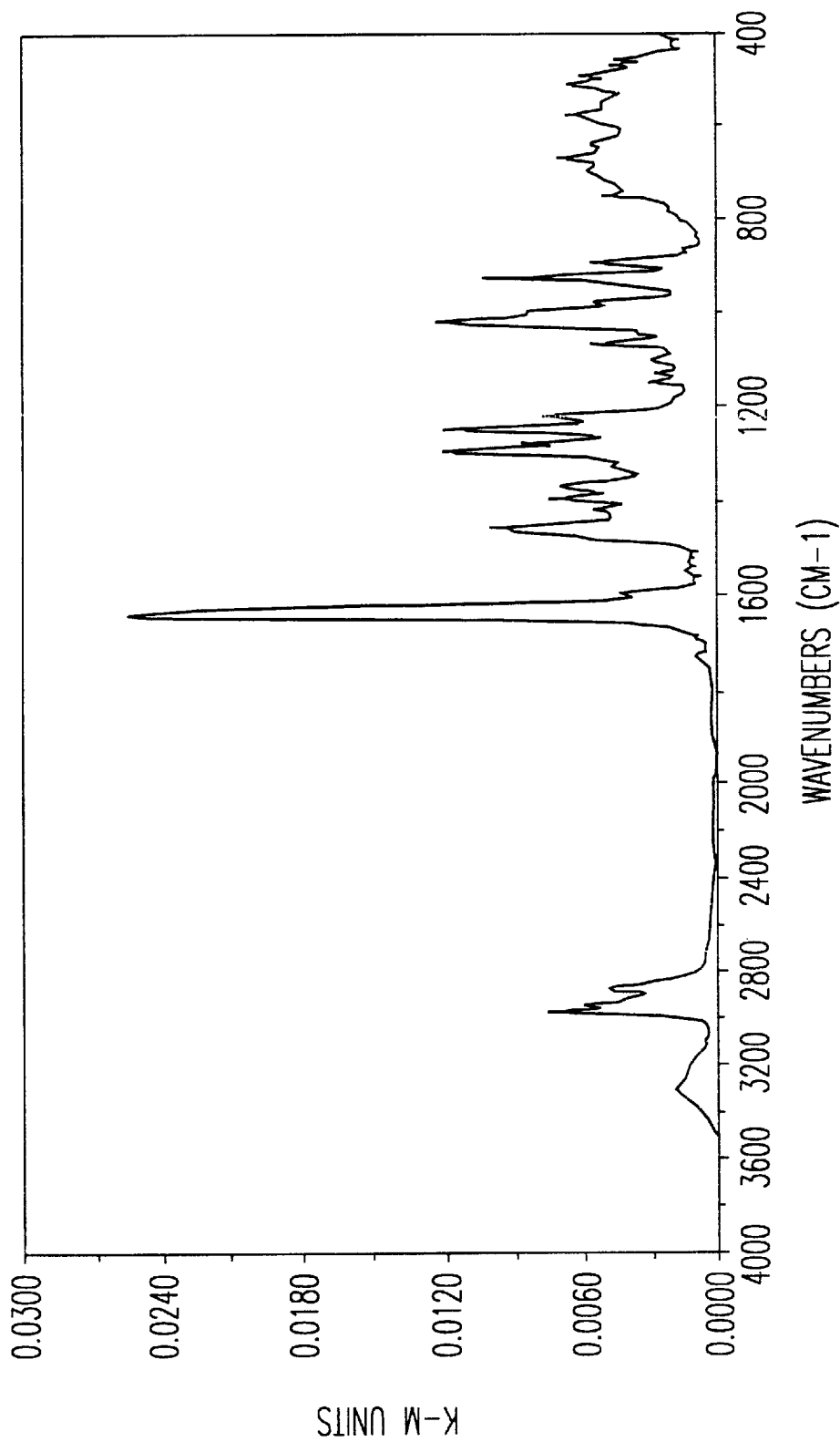
FIG. 3 shows an infrared absorption spectrum of phytocassane C according to the present invention.
Figure 4:
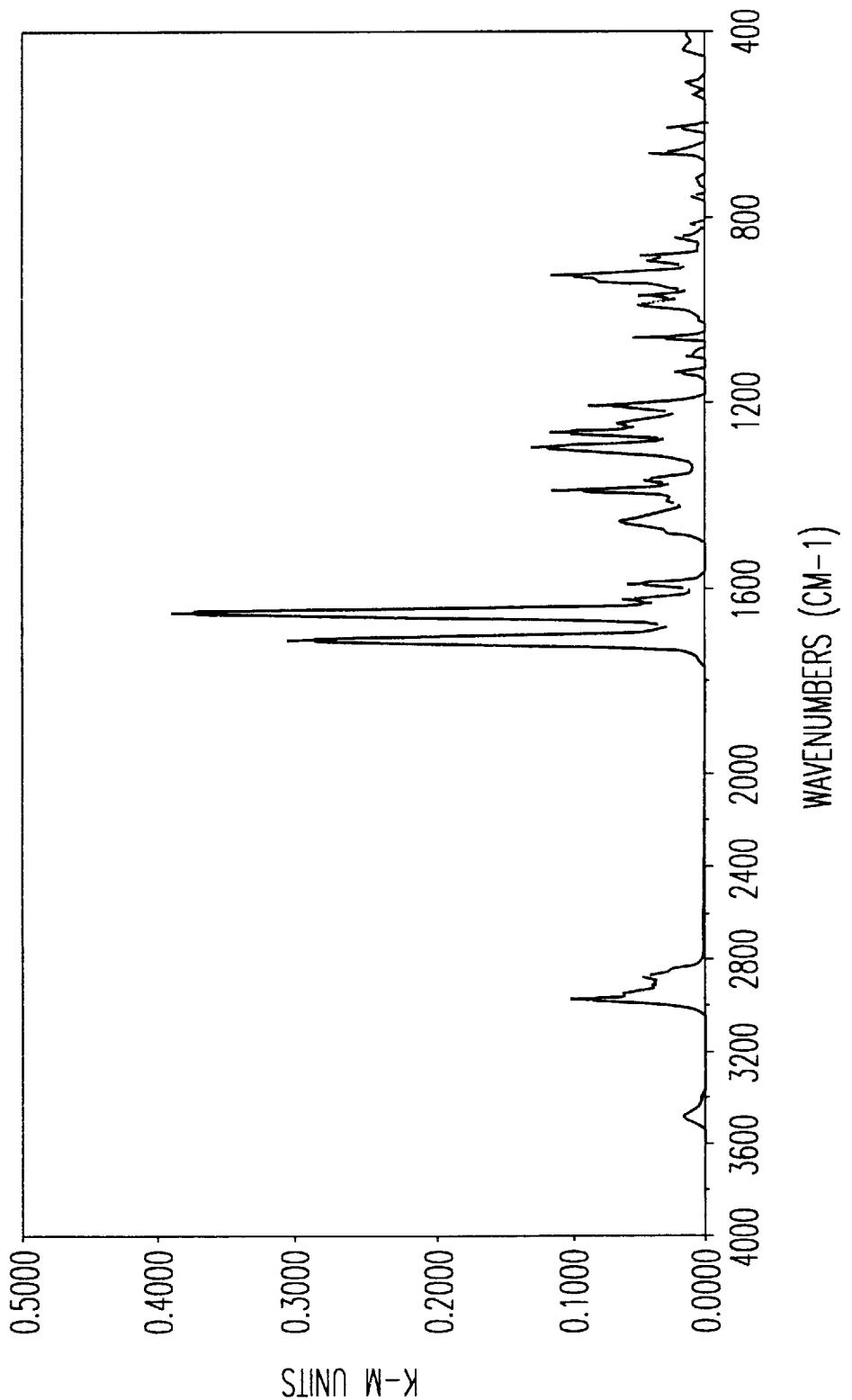
FIG. 4 shows an infrared absorption spectrum of phytocassane D according to the present invention.
Figure 5:
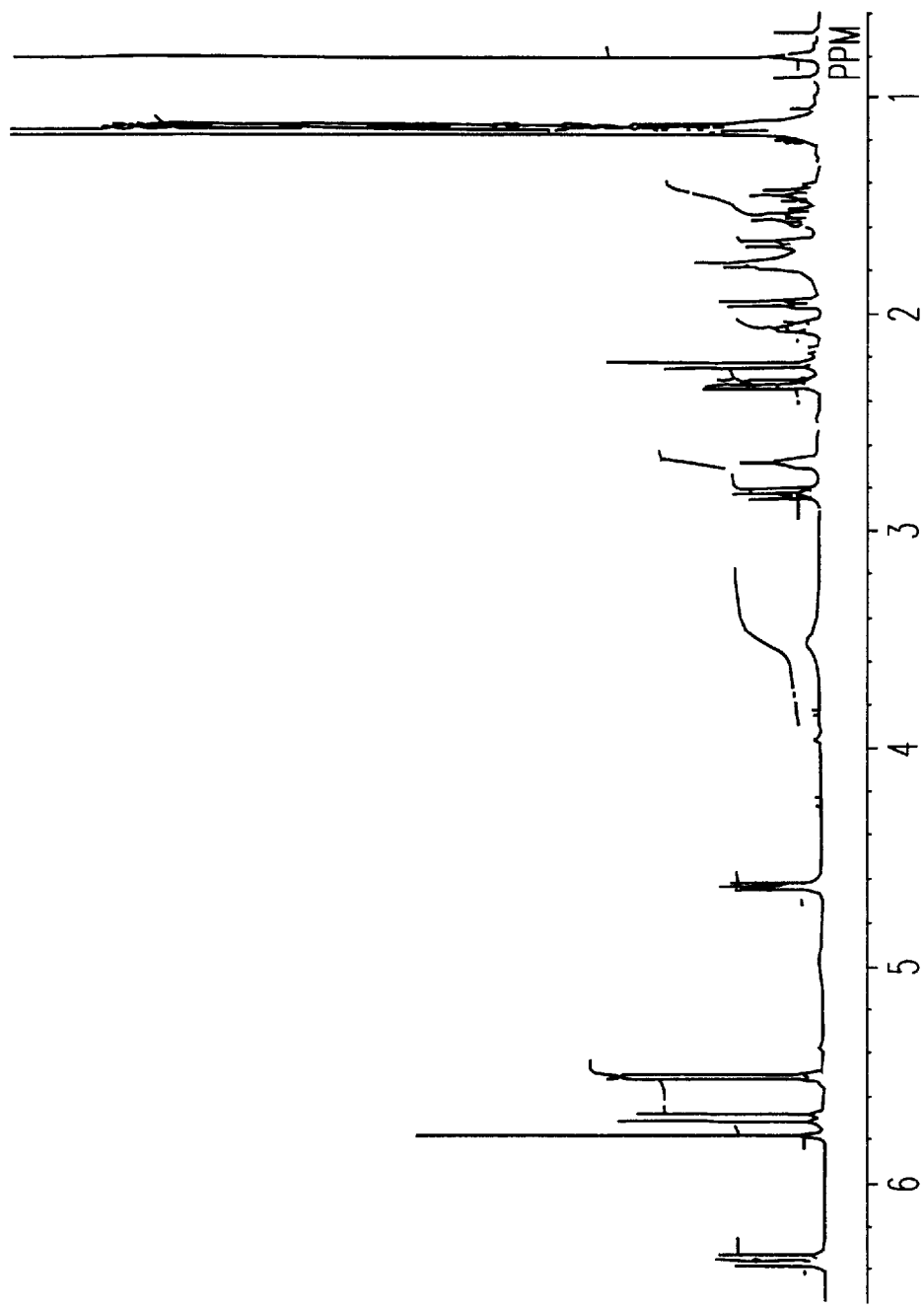
FIG. 5 shows an $^1$H-NMR spectrum of phytocassane A according to the present invention.
Figure 6:
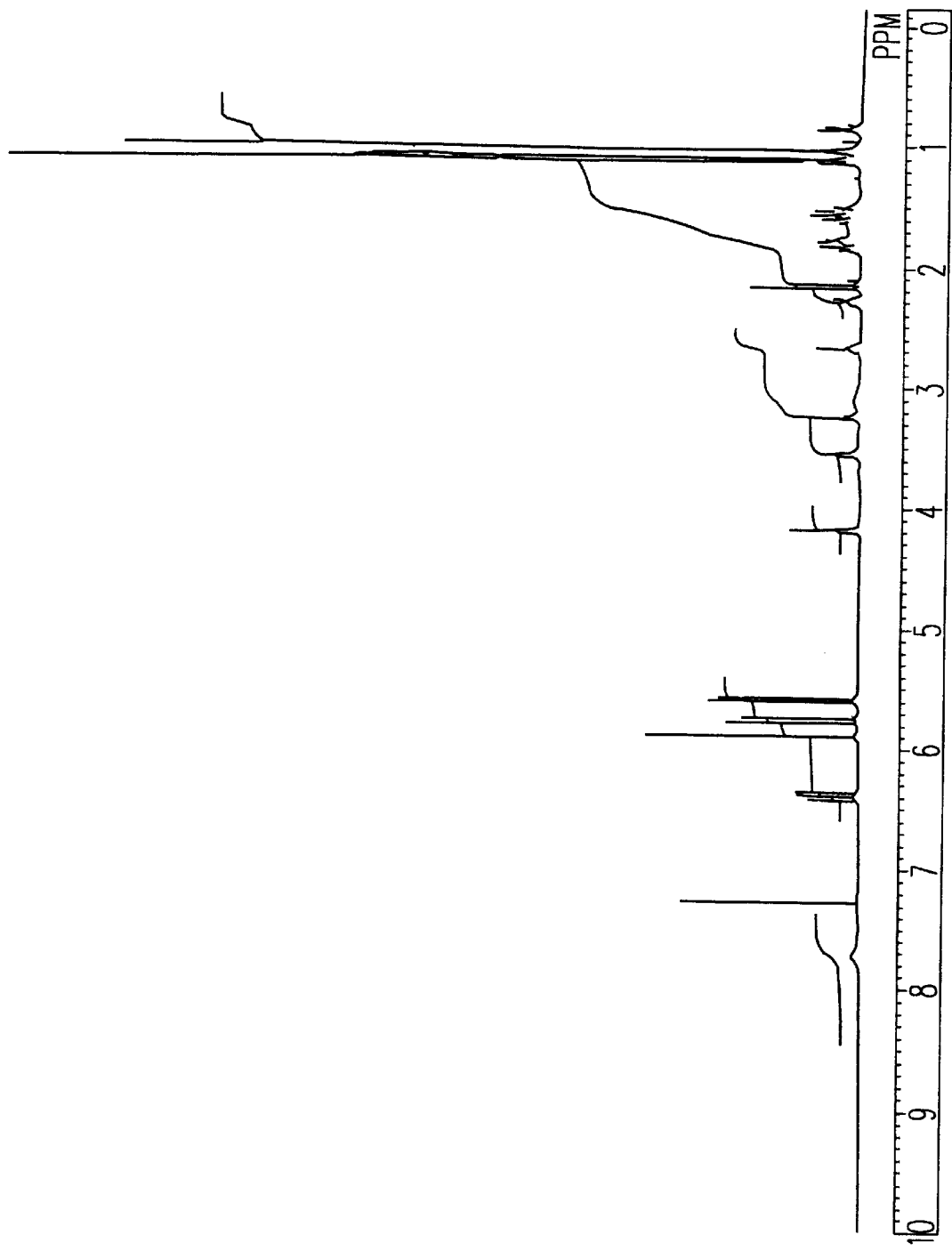
FIG. 6 shows an $^1$H-NMR spectrum of phytocassane B according to the present invention.
Figure 7:
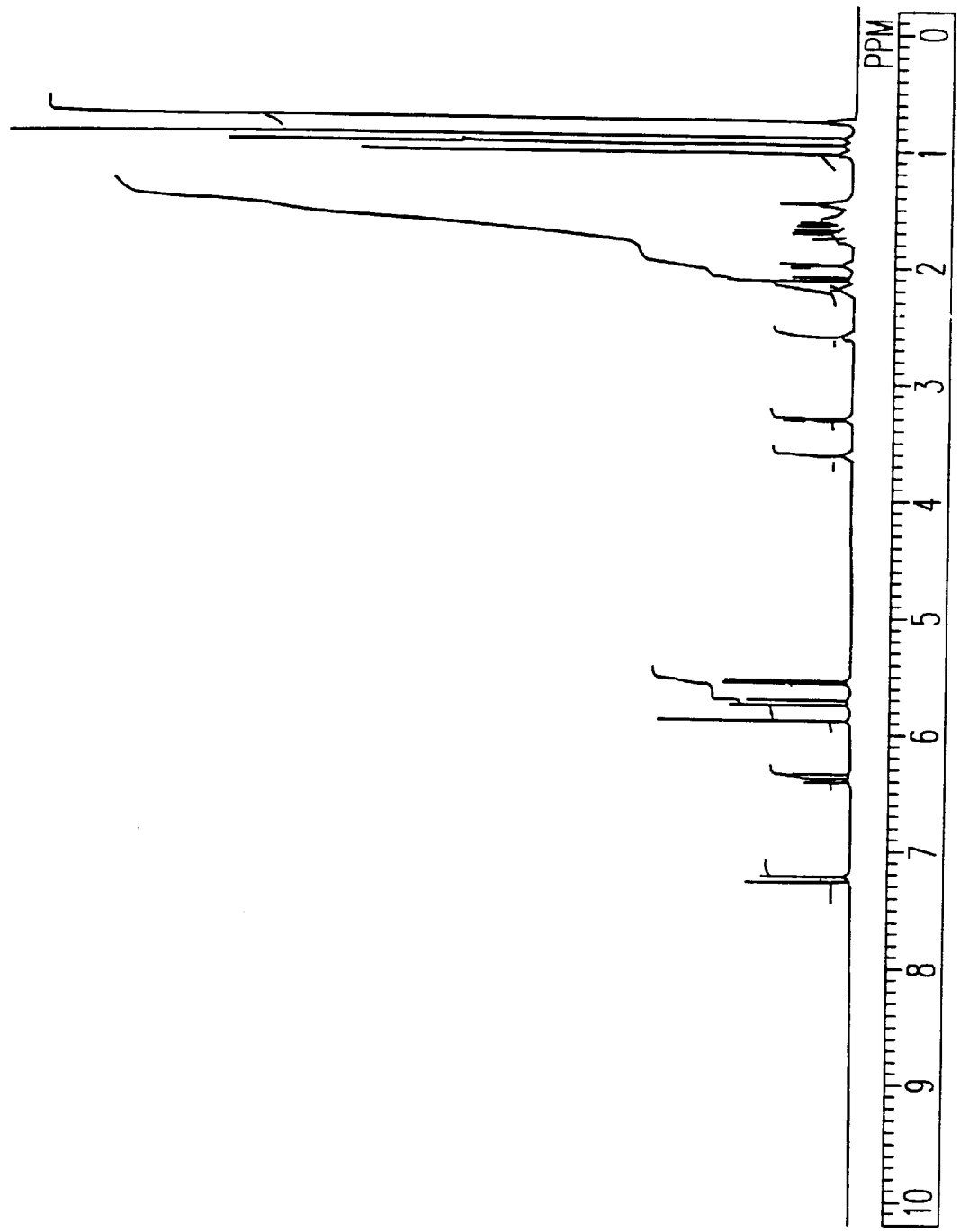
FIG. 7 shows an $^1$H-NMR spectrum of phytocassane C according to the present invention.
Figure 8:
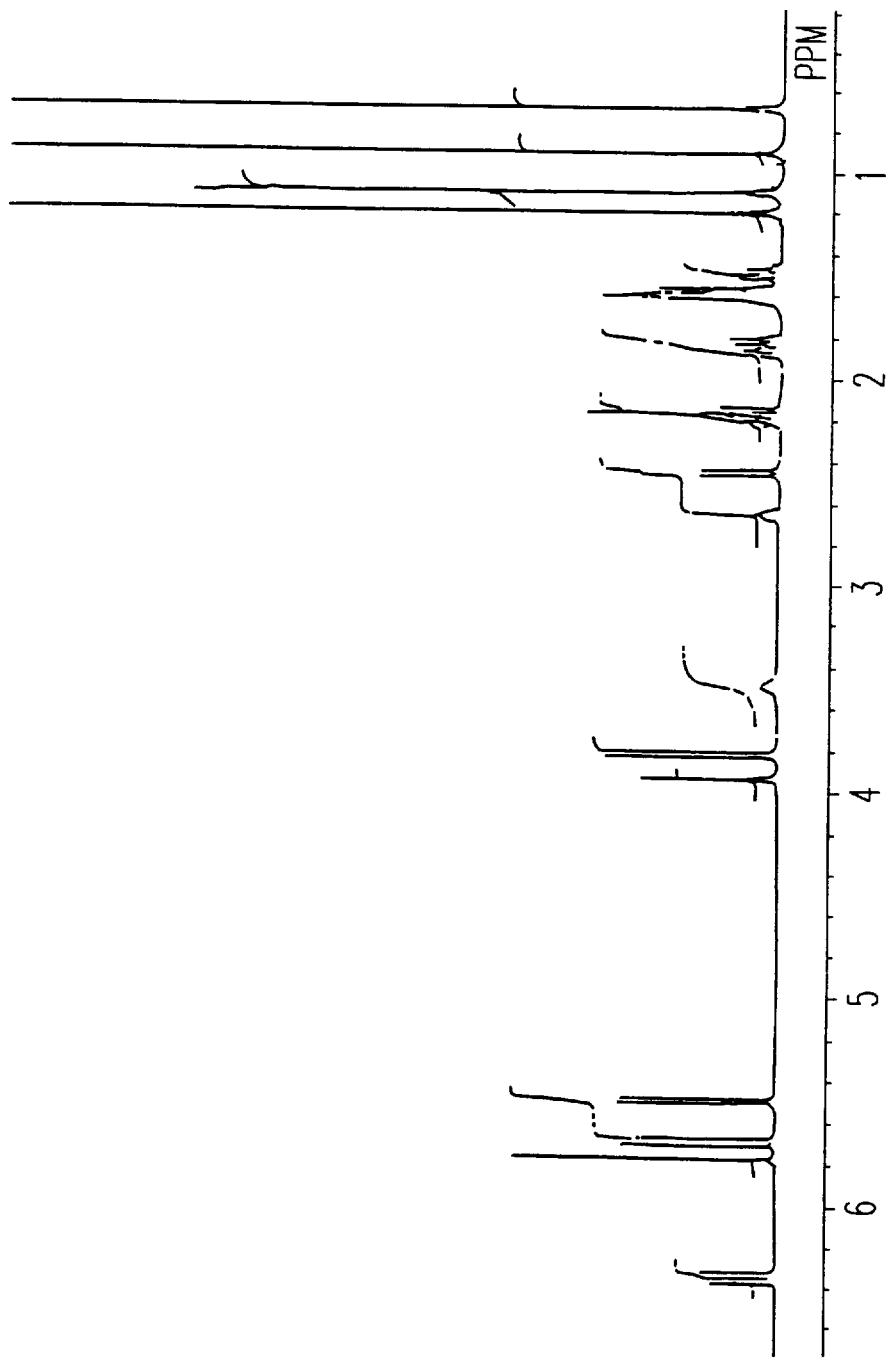
FIG. 8 shows an $^1$H-NMR spectrum of phytocassane D according to the present invention.
Figure 9:
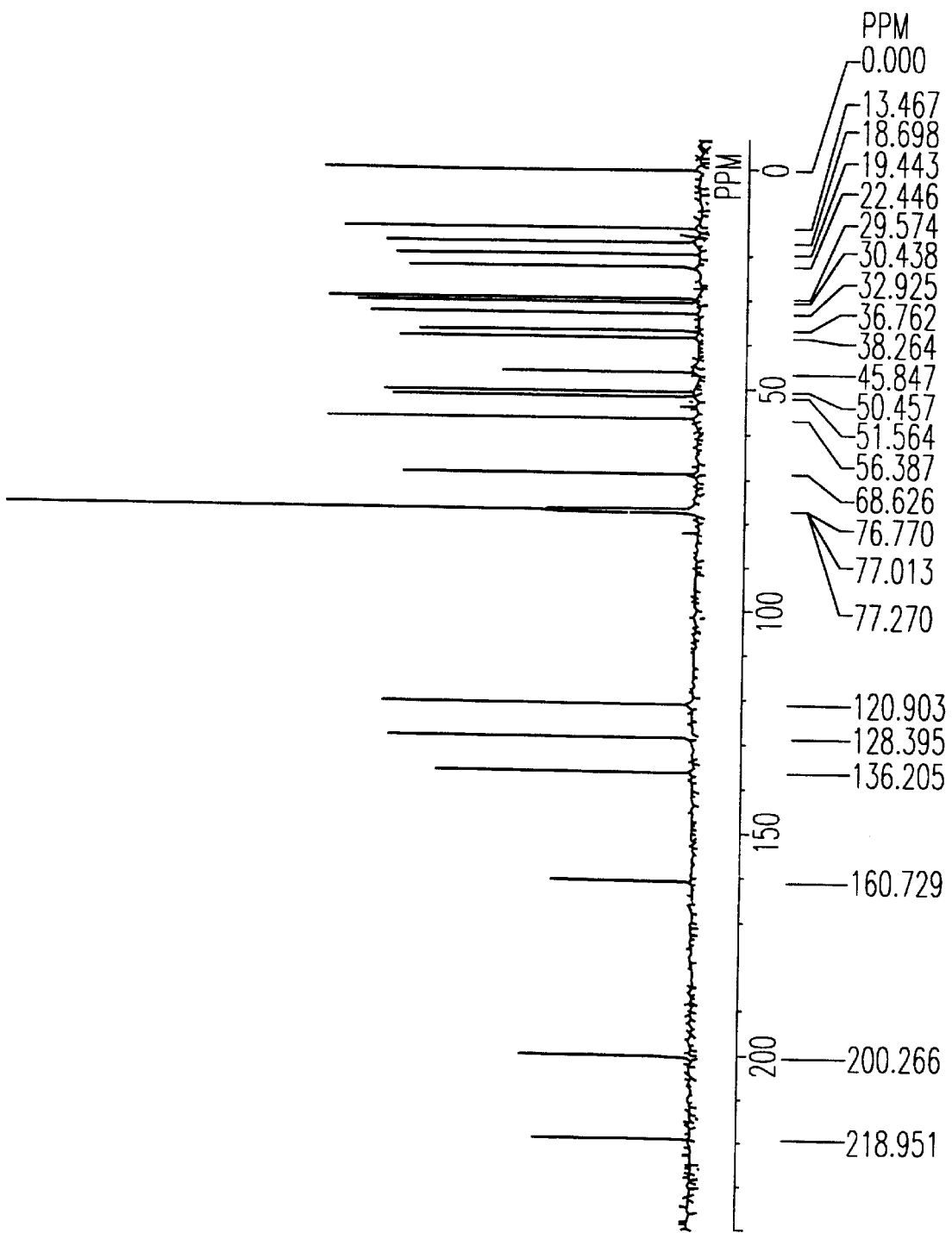
FIG. 9 shows a $^{13}$C-NMR spectrum of phytocassane A according to the present invention.
Figure 10:
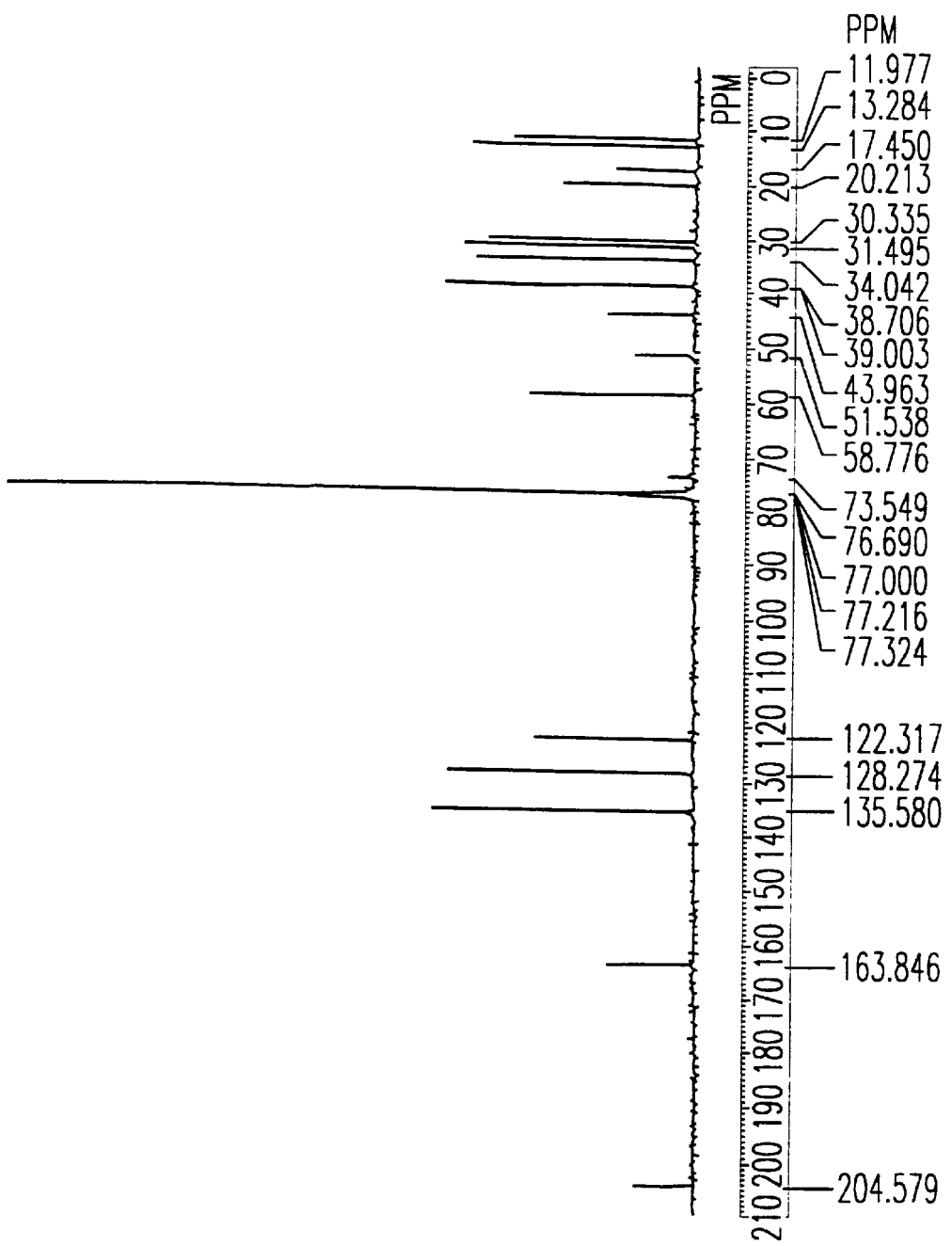
FIG. 10 shows a $^{13}$C-NMR spectrum of phytocassane B according to the present invention.
Figure 11:
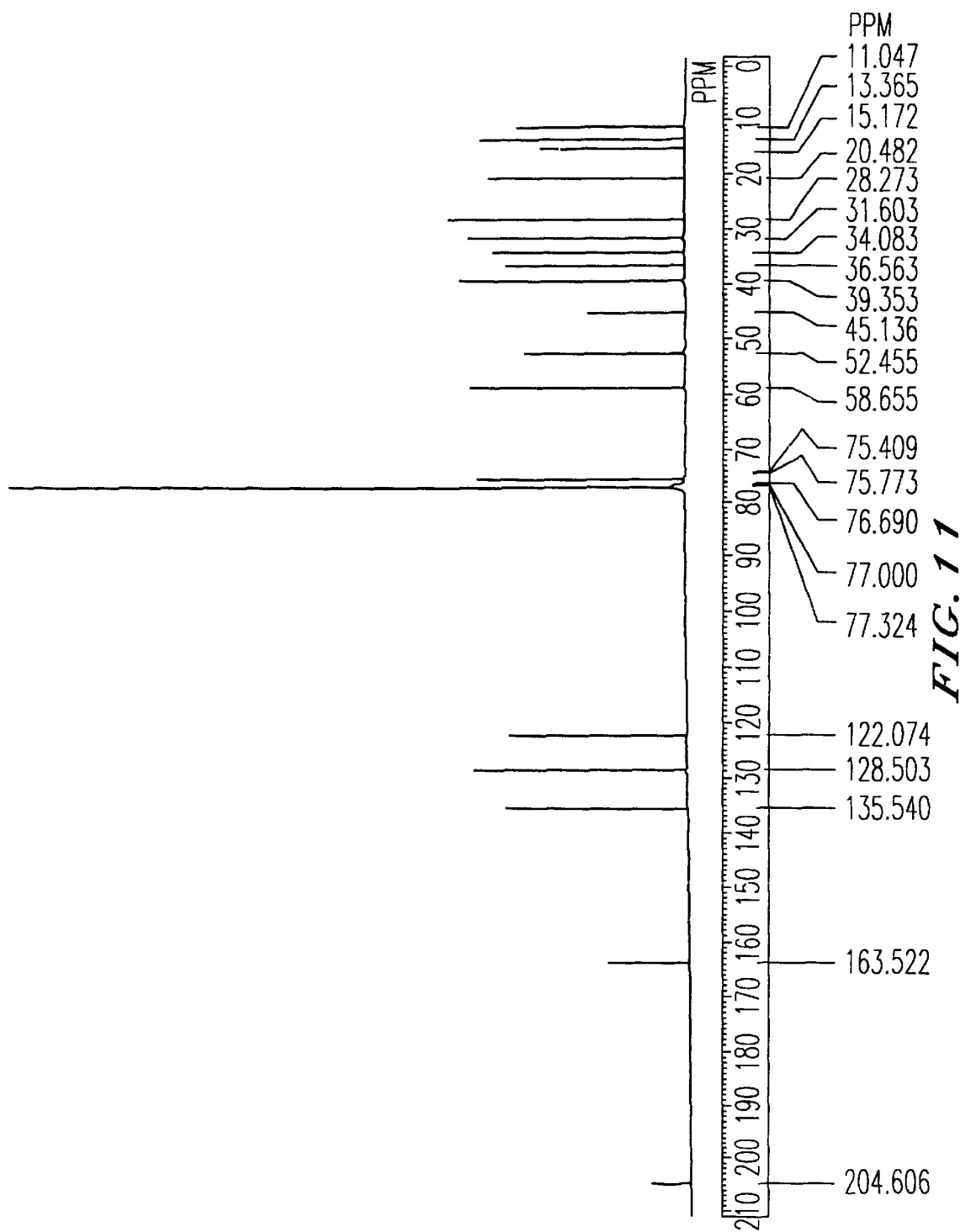
FIG. 11 shows a $^{13}$C-NMR spectrum of phytocassane C according to the present invention.
Figure 12:
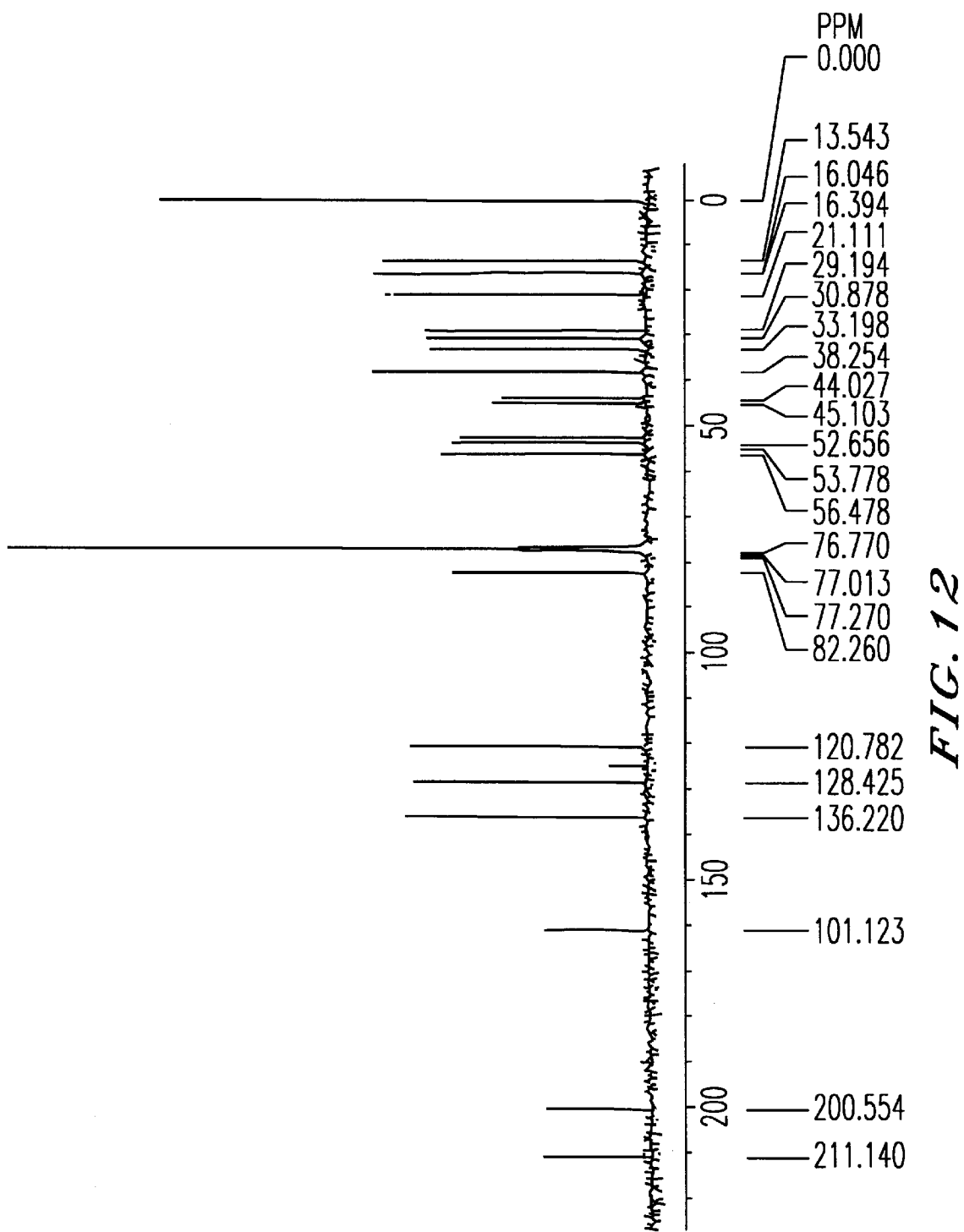
FIG. 12 shows a $^{13}$C-NMR spectrum of phytocassane D according to the present invention.
Figure 13:
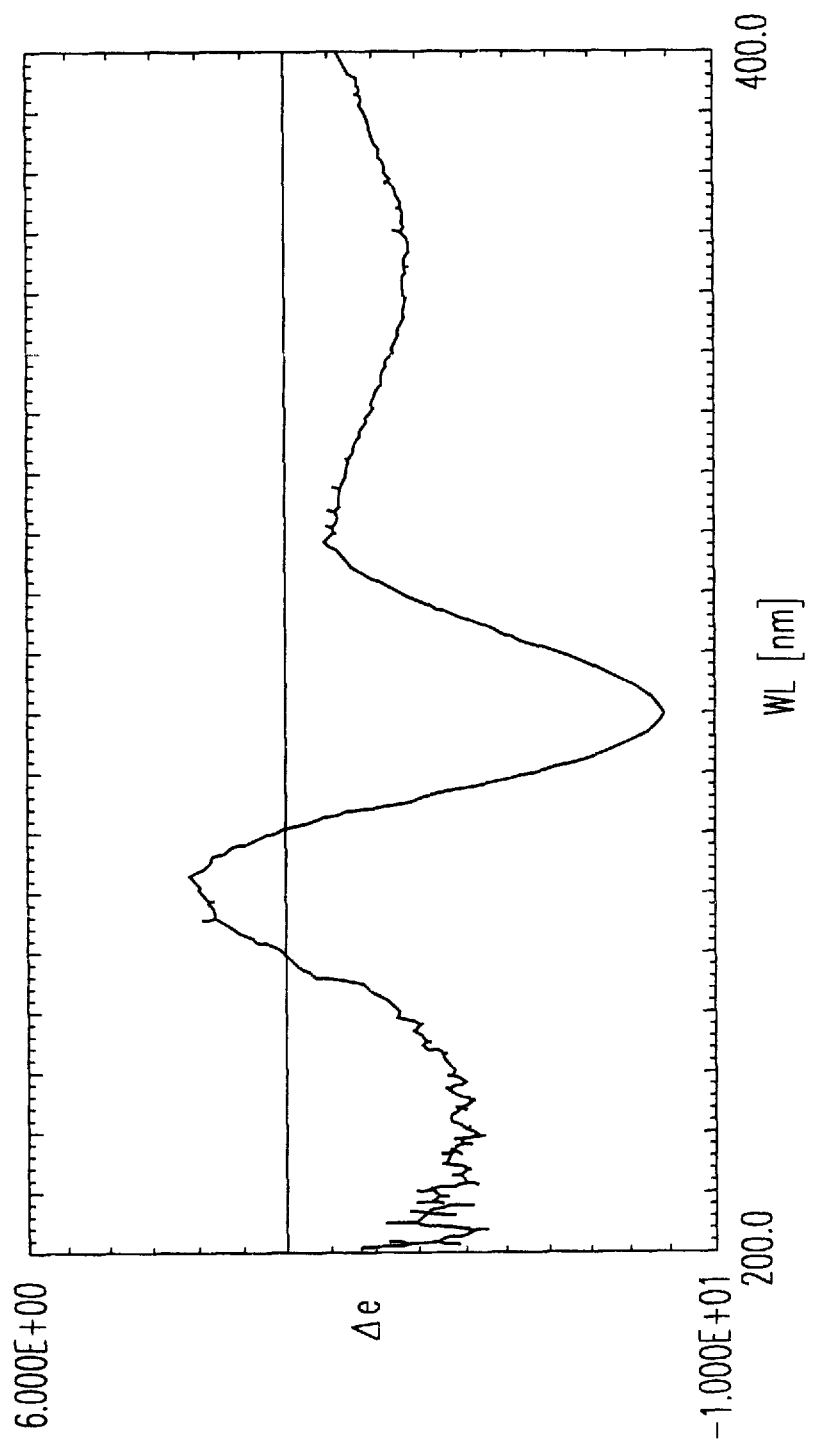
FIG. 13 shows a CD spectrum of phytocassane A according to the present invention.
Figure 14:
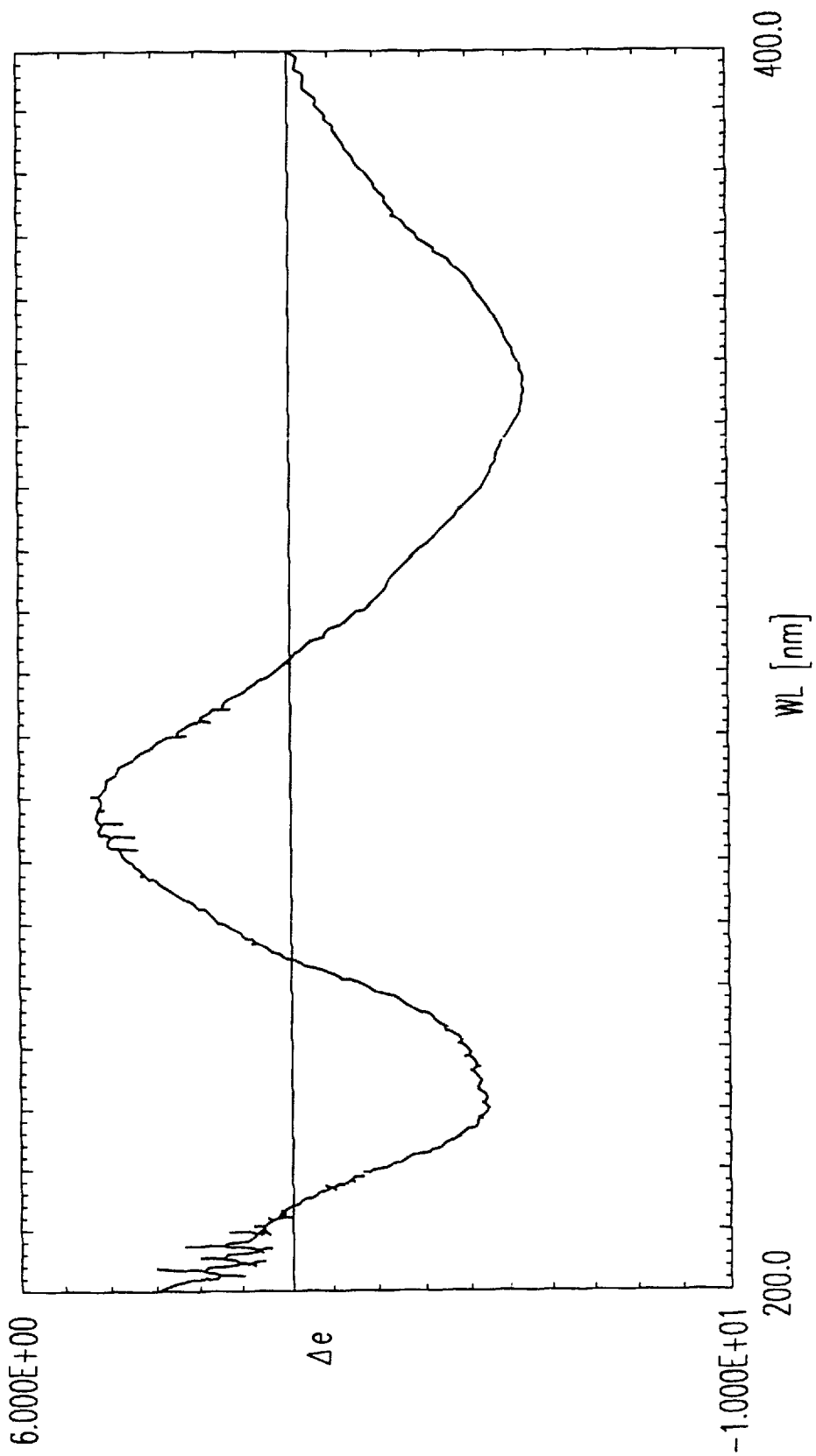
FIG. 14 shows a CD spectrum of phytocassane B according to the present invention.
Figure 15:
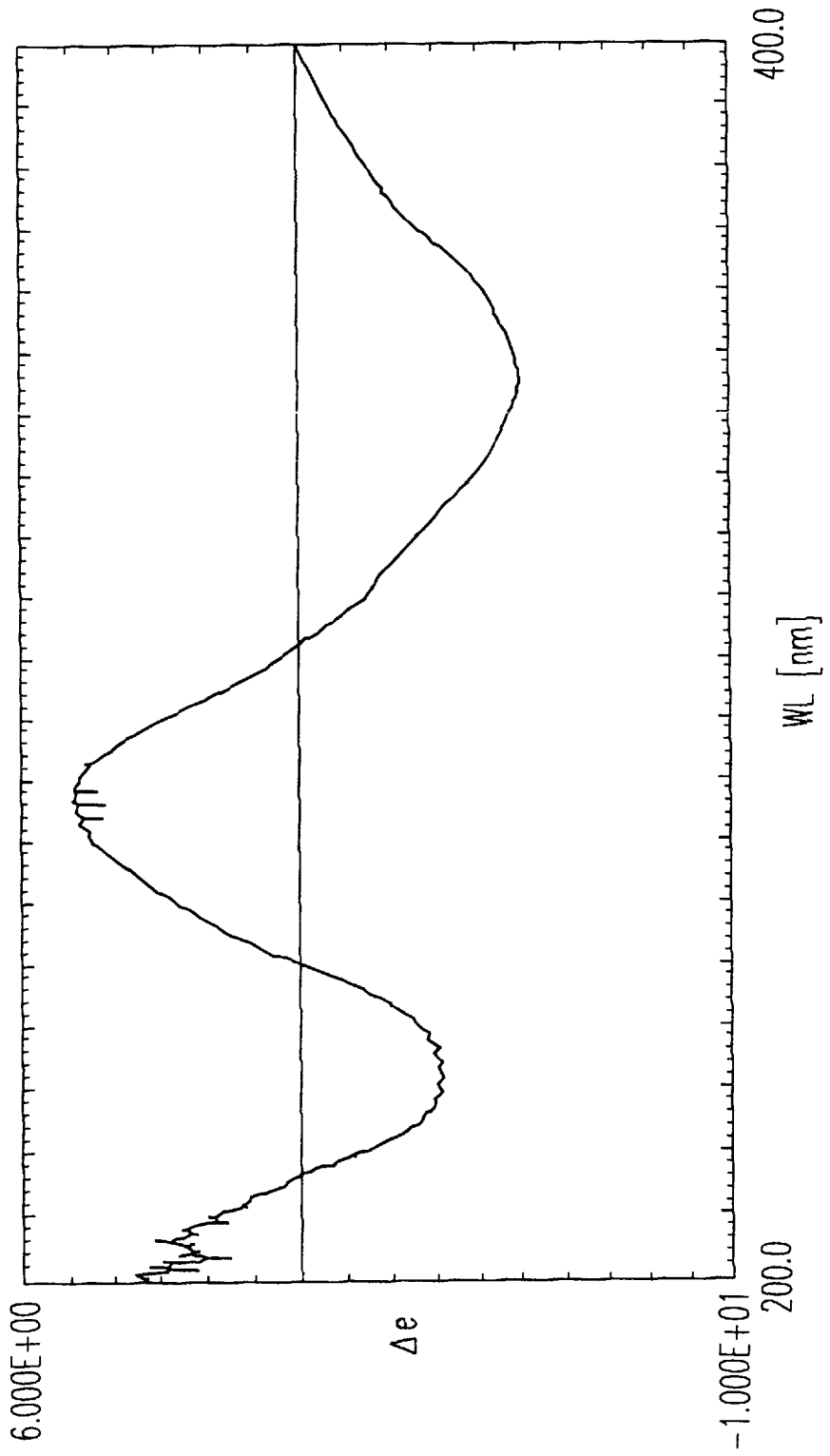
FIG. 15 shows a CD spectrum of phytocassane C according to the present invention.
Figure 16:
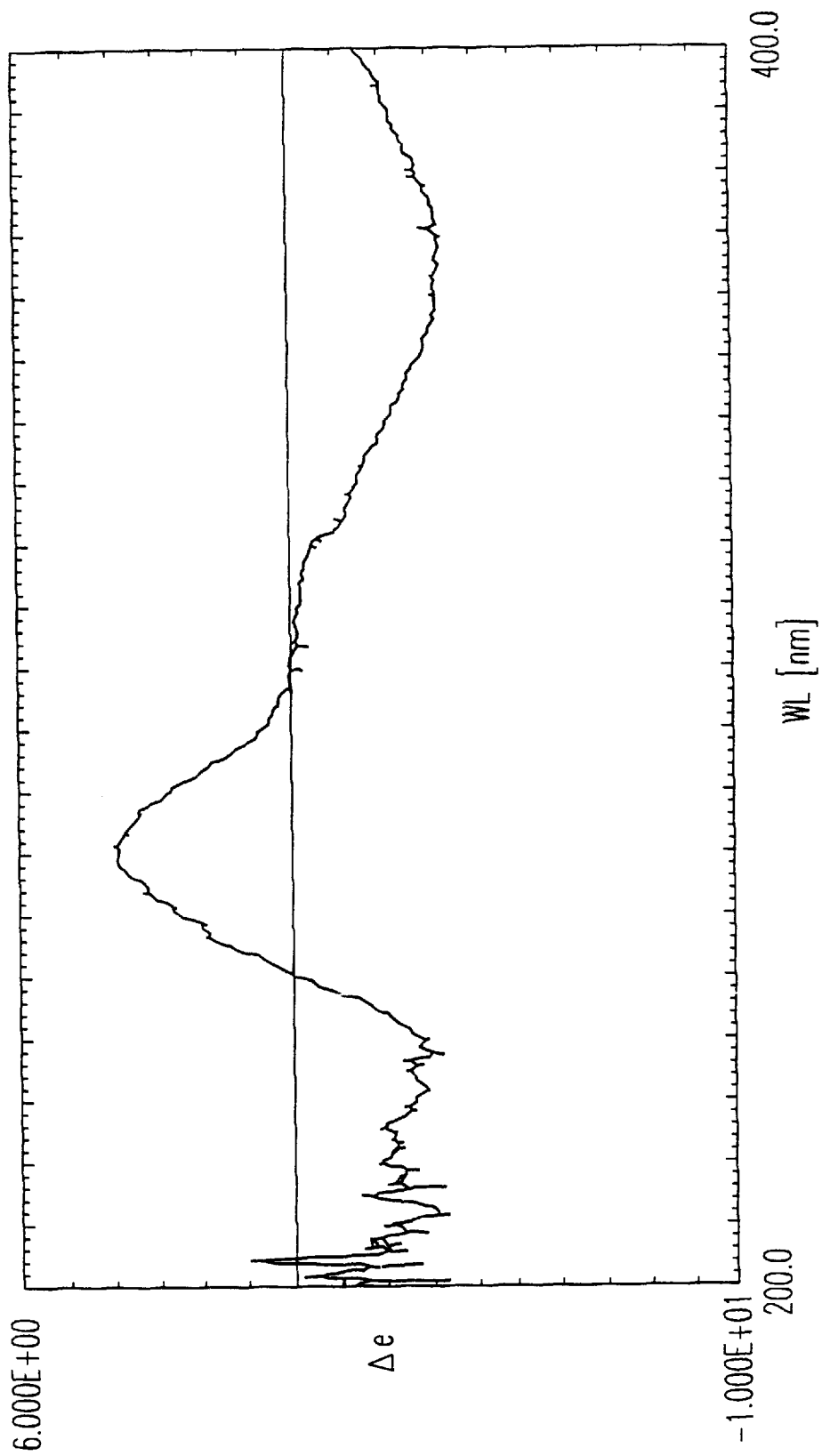
FIG. 16 shows a CD spectrum of phytocassane D according to the present invention.
Figure 17:
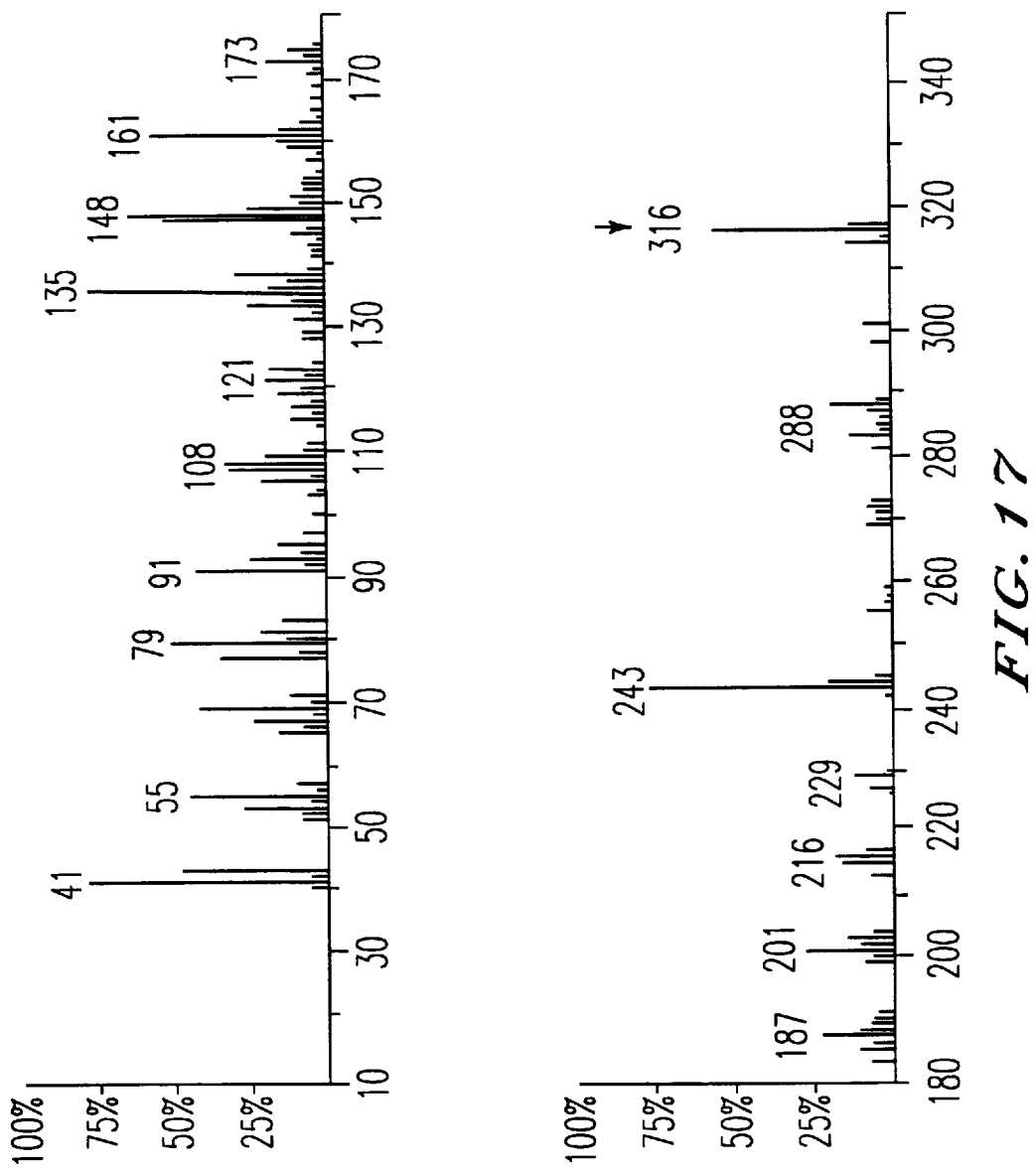
FIG. 17 shows a mass spectrum of phytocassane A according to the present invention.
Figure 18:
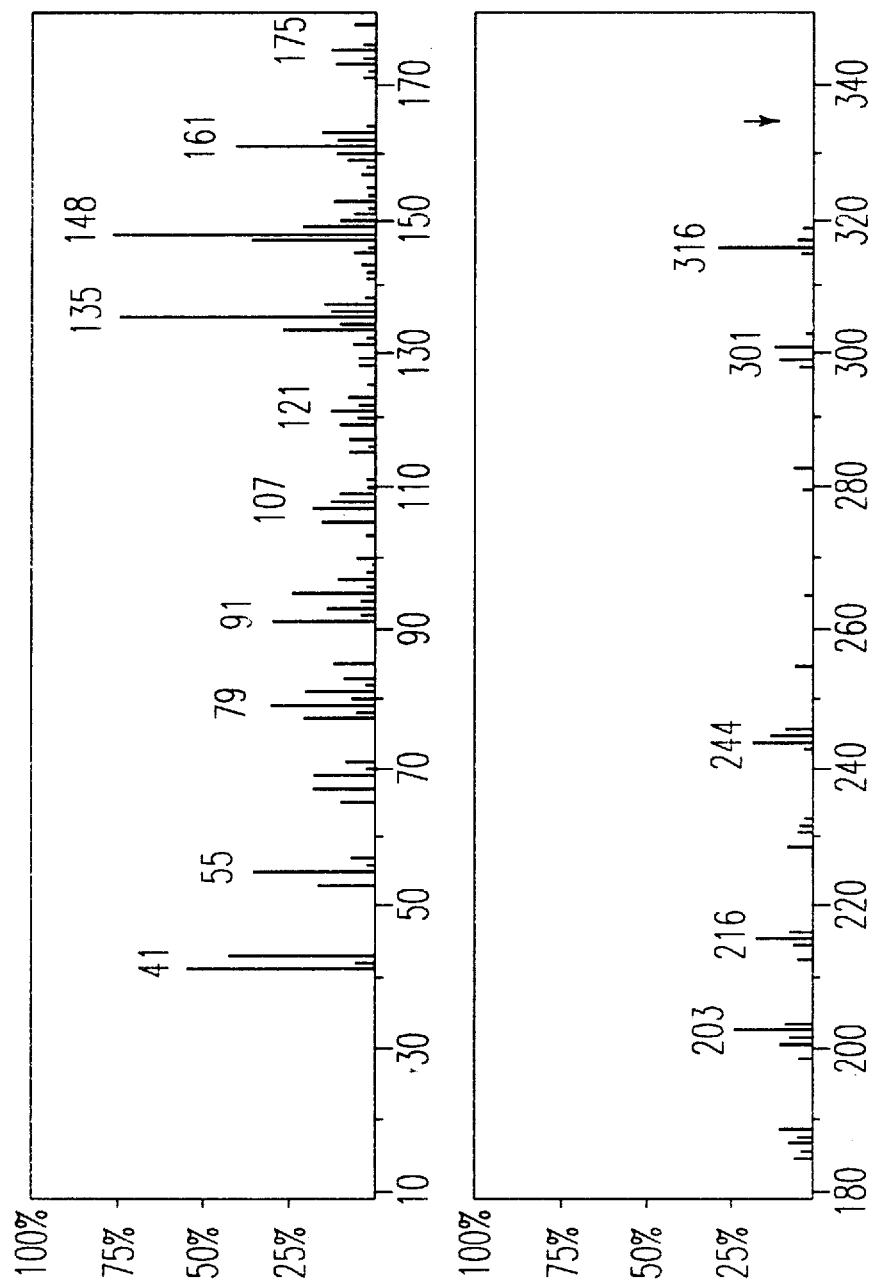
FIG. 18 shows a mass spectrum of phytocassane B according to the present invention.
Figure 19:
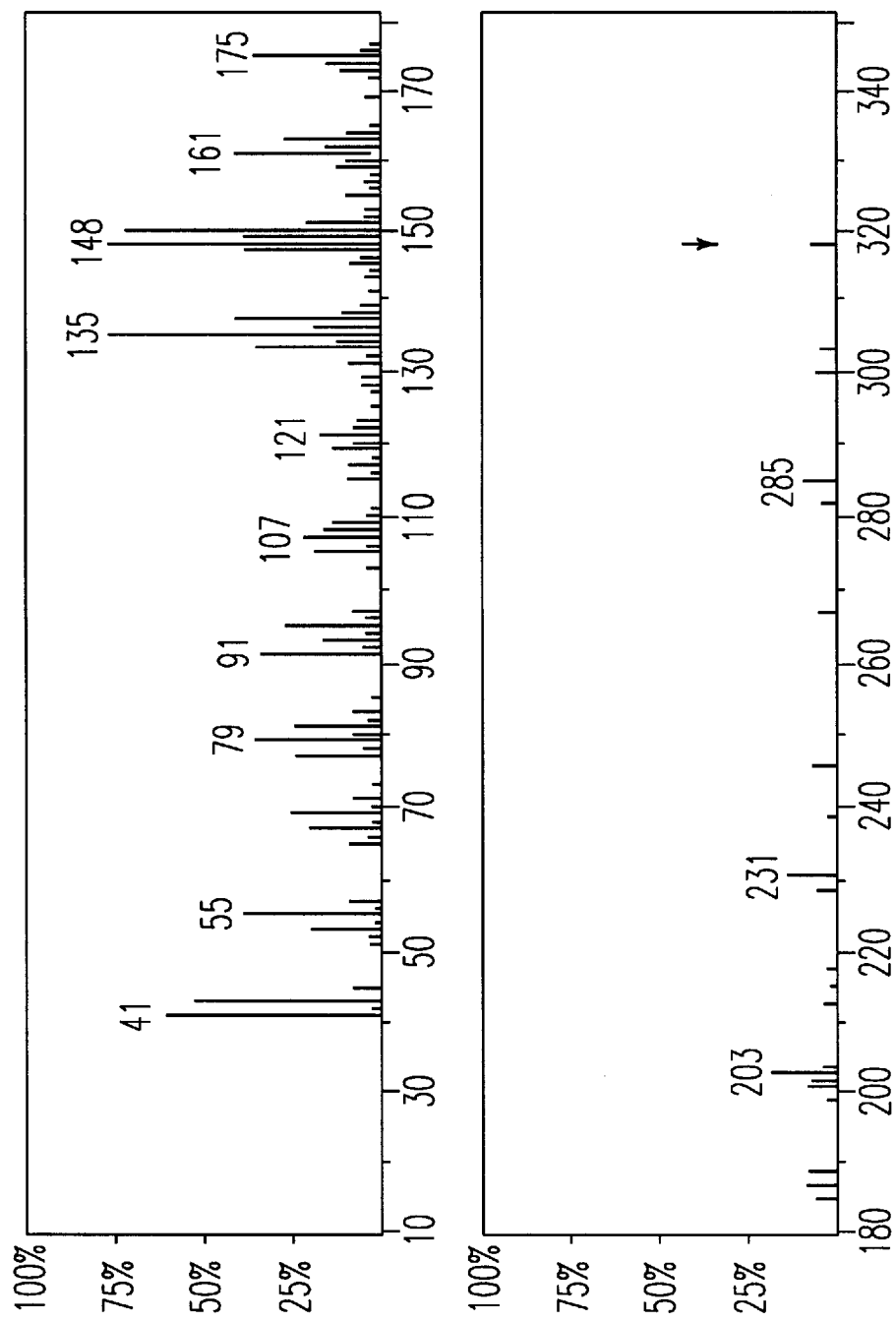
FIG. 19 shows a mass spectrum of phytocassane C according to the present invention.
Figure 20:
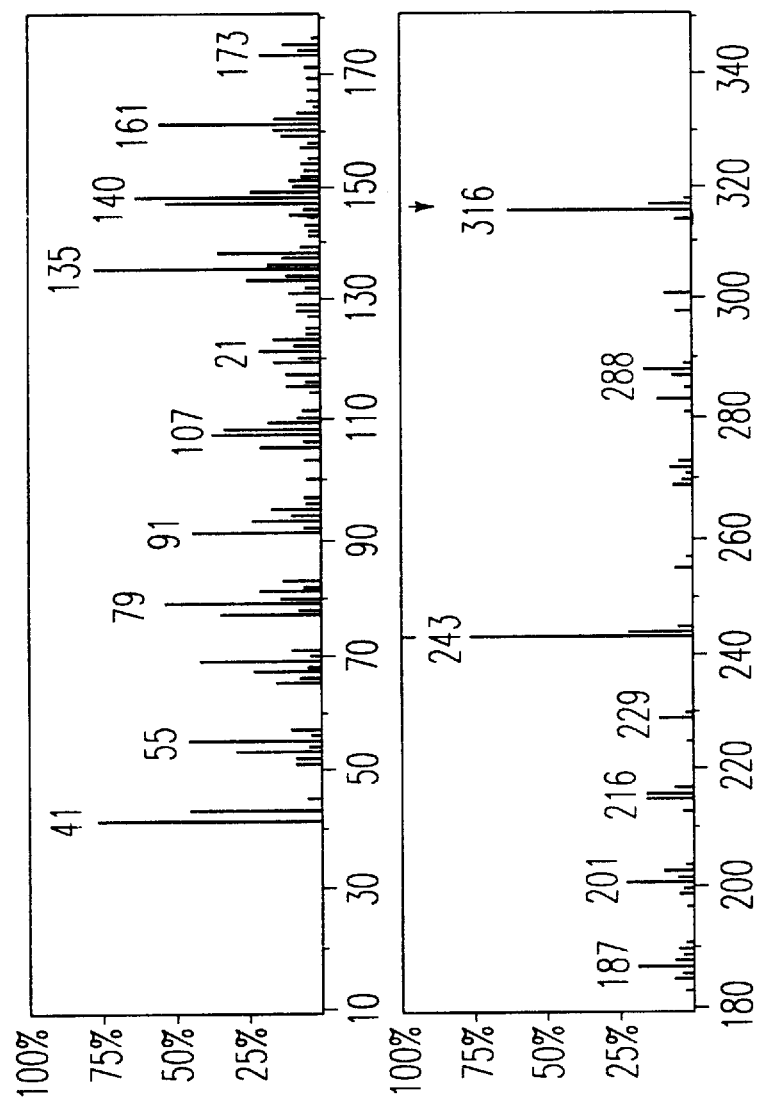
FIG. 20 shows a mass spectrum of phytocassane D according to the present invention.

Hereunder, the present invention will be described more specifically according to Examples; however, the present invention is not restricted to said Examples at all.

EXAMPLE 1
(Isolation of phytocassanes A, B, C and D)

Stems (2 kg) of a rice plant (Koshihikari) infected with *Rhizoctonia solani* (rice sheath blight fungus) were collected; after they were extracted with ethyl acetate, the extract ingredient was adsorbed onto Sep Pack C-18 manufactured by Millipore Limited and eluted with 40% ethanol to isolate a phytocassane fraction. Subsequently, it was used as a sample and purified according to a three-step isolation operation by high performance liquid chromatography (HPLC). As the first step, the sample was introduced into TSKgel ODS-120A manufactured by Toso and eluted with 52.5% ethanol to isolate phytocassane fractions. As the second step, the sample was introduced into TSKgel ODS-120A manufactured by Toso and eluted with 60% acetonitrile to isolate phytocassane fractions. As the third step, the sample was introduced into TSKgel ODS-120T manufactured by Toso and eluted with 50% acetonitrile to isolate phytocassanes B and C, eluted with 55% acetonitrile to isolate a phytocassane A, and eluted with 60% acetonitrile to isolate a phytocassane D, respectively. The retention time (minutes) of phytocassanes A, B, C and D under the column conditions of each step is shown in Table 1

TABLE 1

Isolation of Phytocassanes A, B, C and D by HPLC

| Column conditions | Retention time (minutes) | | | |
| --- | --- | --- | --- | --- |
| | Phytocassane A | Phytocassane B | Phytocassane C | Phytocassane D |
| ODS-120A 52.5% ethanol | 38 | 44 | 44 | 44 |
| ODS-120A 60% acetonitrile | 37 | 37 | 37 | 44 |
| ODS-120T 50% acetonitrile | | 48 | 45 | |
| ODS-120T 55% acetonitrile | 45 | | | |
| ODS-120T 60% acetonitrile | | | | 44 |

According to fractionating by the above three-step high performance liquid chromatography (HPLC), about 20 mg of phytocassane A, about 10 mg of phytocassane B, about 3 mg of phytocassane C and about 8 mg of phytocassane D were obtained as a single phytocassane fraction.

The infrared absorption spectra, $^1$H-NMR spectra, $^{13}$C-NMR spectra and CD spectra of phytocassanes A, B, C and D are shown in FIGS. 1–16.

EXAMPLE 2

(Test for protecting effects on infection of rice blast fungus)

Rice seeds (Variety: Jukkoku) were sowed in pots filled with culture soil at the rate of 8 seeds per pot, and were cultivated till the period developing 4 or 5 leaves, and three sections were subjected to a test, making 12 pots one section. A solution of phytocassane A with a concentration of 6 ppm and a solution of phytocassane B with a concentration of 3 ppm were prepared with water containing 500 ppm of Tween 20. Water and each sample solution in an amount of 30 ml respectively were sprayed onto the rice plant of each section, and the rice plant was left to stand at room temperature for 4 hours to dry leaves. After 50 ml of a spore suspension of the Pyricularia oryzae race 007 strain (strain having affinity) were sprayed onto the leaves of each section, they were left to stand for 24 hours under the conditions of moistening and darkness to perform an inoculation treatment. Then, they were transferred into an artificial weather room to cultivate; 5 days after, the number of infected leaves and the number of non-infected leaves of each section were counted to compare the degree of the outbreak of rice blast disease. The results are shown in Table 2

TABLE 2

| Sample section | Non-infected leaves (No.) | Infected leaves (No.) | Outbreak of disease (%) |
| --- | --- | --- | --- |
| Control | 178 | 88 | 49 |
| Phytocassane A | 178 | 54 | 30 |
| Phytocassane B | 184 | 36 | 20 |

In the water-treated section, the number of non-infected leaves was 178, the number of infected leaves was 88 and the rate of the outbreak of the disease was 49%; in phytocassane A, while the number of non-infected leaves was 178, the number of infected leaves was 54 and the rate of the outbreak of the disease was 30%; in phytocassane B, while the number of non-infected leaves was 184, the number of infected leaves was 36 and the rate of the outbreak of the disease was 20%; thus, it was confirmed clearly that phytocassanes A and B have an effect of inhibiting the outbreak of rice blast disease. As a result of performing the same test about phytocassanes C and D, almost the same results were obtained.

EXAMPLE 3

(Test for inhibitory effects on hypha extension of rice blast fungus)

A suspension of spores of rice blast fungus (*Pyricularia oryzae* race 007) and water containing 100 ppm of Tween 20 was prepared, and 25 µl thereof were put on a hole object glass plate. The spores on the plate were cultured at 28° C. for 6 hours to germinate. Separately, phytocassane samples were dissolved in water containing 500 ppm of Tween 20 in prescribed concentrations. To the suspensions of the germinated spores on the plate were added 25 µl of the aqueous phytocassane solutions with prescribed concentrations respectively to prepare sample sections, and to the suspension was added 25 µl of water containing 500 ppm of Tween 20 to prepare a control section; they were cultured at 28° C. overnight, and the state of the hypae extension of each section was observed with a microscope. The Results are shown in Table 3.

TABLE 3

| Sample section | Phytocassane concentration (ppm) showing a length of a hypha of about 50% of that of the control section |
| --- | --- |
| Control | — |
| Phytocassane A | 10 |
| Phytocassane B | 3 |
| Phytocassane C | 6 |
| Phytocassane D | 20 |

The sample concentration of the sample sections showing a length of a hypha of about 50% of that of the control section was 10 ppm in phytocassane A, 3 ppm in phytocassane B, 6 ppm in phytocassane C and 20 ppm in phytocassane D.

EXAMPLE 4

(Test for inhibitory effects on hypha extension of rice sheath blight fungus)

A commercially available potato dextrose agar medium (3.9 g) (manufactured by Eiken Kagaku) was dissolved in 100 ml of water and 2 ml thereof were poured into each test tube, sterilized by an autoclave at 121° C. for 15 minutes and cooled to 60° C. Separately, a phytocassane sample was dissolved in water containing Tween 20 of 500 ppm in a prescribed concentration and subjected to filtration in aseptic condition. The phytocassane solutions were added into the agar medium solution, mixed homogeneously and introduced into chalets to prepare agar plates containing the samples with prescribed concentrations. As a control, a blank plate was prepared by adding water containing no phytocassane sample and containing a corresponding amount of Tween 20 of 500 ppm to the agar medium.

A fragment of the rice sheath blight fungus (Rhizoctonia solani) cultured agar medium was put on the center of each chalet plate and cultured at 28° C. and the extension of hyphae of each sample after 40 hours was observed. The results are shown in Table 4. Hyphae of each sample extended centering around the central inoculated points on the plate to form fungal mass.

TABLE 4

| Sample section | Phytocassane concentration (ppm) | Diameter of a fungal mass (mm) |
| --- | --- | --- |
| Control | — | 18 |
| Phytocassane A | 17 | 5 |
| Phytocassane B | 15 | — |
| Phytocassane C | 10 | — |
| Phytocassane D | 50 | 5 |

While the diameter of a fungal mass of the control plate was 18 mm, that of phytocassane A of the 17 ppm section was 5 mm; no extension of hyphae was observed in phytocassane B of the 15 ppm section and phytocassane C of the 10 ppm section. In phytocassane D of the 50 ppm section, the diameter of a fungal mass was about 5 mm.

EXAMPLE 5

(Preparation of antifungal terpene compounds)

1) Formation of rice calluses

The embryo and albumen parts of rice (Koshihikari) seeds from which rice husks had been removed were sterilized with a 70% ethanol solution and a 1% hypochlorite soda solution, and then planted in the DK medium from which aspartic acid and glutamine had been removed and to which a double amount of 1,4-D and 1% of agarose had been added. Thirty days later, calluses derived were transferred into a liquid medium.

2) Proliferation of rice calluses

Rice (Koshihikari) calluses were subjected to rotary shaking culture (90 rpm, 25° C., 3,000 lux) in the DK medium (liquid medium containing the following; in 1 L, 30 g of sucrose, 0.809 g of $KNO_3$, 0.066 g of $(NH_4)SO_4$, 0.312 g of $NaH_2PO_4 \cdot 2H_2O$, 0.148 g of $CaCl_2 \cdot 2H_2O$, 0.246 g of $MgSO_4 \cdot 7H_2O$, 0.02 g of Fe-EDTA, 0.101 g of vitamins, 2 mg of glycine, 0.7 g of aspartic acid, 0.7 g of glutamine, 1 mg of 2,4-D, and other salts of $MnSO_4 \cdot 4\text{–}6H_2O$, $ZnSO_4 \cdot 7H_2O$, $CuSO_4 \cdot 5H_2O$, $Na_2MoO_4 \cdot 2H_2O$ and $H_3BO_3$ in required amounts) under the conditions of a pH of 5.8, 25° C. and 14 days. A proper amount of calluses were sampled and crushed finely by a spatula, and only calluses passing through a 20-mesh sieve were selected.

3) Production of phytocassanes

The sieved calluses were put into a 500-milliliter Erlenmeyer flask and 90 ml of the DK medium were added thereto and subjected to rotary shaking culture (90 rpm, 25° C., 3,000 lux) for two days; subsequently, 1 ml of a cellular extract ingredient solution of potato pathogenic fungi filtrated in aseptic condition was added into the culture broth, and the resultant culture broth was further subjected to rotary shaking culture for 4 days. After the completion of the culture, the culture broth was subjected to centrifugal separation (12,000 rpm); the same amount of ethyl acetate was added into the obtained supernatant to extract phytocassanes and the extract was concentrated to dry it under vacuum. A proper amount of the concentrate was dissolved in a 40% ethanol solution and analyzed by high performance liquid chromatography; as a result, the amount of each phytocassane was as shown in Table 5.

TABLE 5

| Kind of phytocassane | Yield of phytocassane ug/culture supernatant 1 ml |
|---|---|
| Phytocassane A | 6.3 |
| Phytocassane B | 0.6 |
| Phytocassane C | 15.4 |
| Phytocassane D | 1.2 |

After each phytocassane was fractioned by HPLC, the corresponding peak portion was collected and concentrated to dry it. The obtained product was dissolved in a small amount of acetone and analyzed by a gas chromatograph mass spectrometer; as a result, a mass spectrum showing the molecular ion peak corresponding to each molecular weight was obtained (FIGS. 17–20). As a result of performing analysis in the same manner employing cellular extract ingredients of Pyricularia oryzae, almost the same results were obtained.

4) Production of momilacones

The sieved calluses were put into a 500-milliliter Erlenmeyer flask and 90 ml of the DK medium were added thereto and subjected to rotary shaking culture (90 rpm, 25° C., 3,000 lux) for two days; subsequently, 1 ml of a cellular extract ingredient solution of potato pathogenic fungi filtrated in aseptic condition was added into the culture broth, and the resultant culture broth was further subjected to rotary shaking culture for 4 days. After the completion of the culture, the culture broth was subjected to centrifugal separation (12,000 rpm); the same amount of ethyl acetate was added into the obtained supernatant to extract momilactones and the extract was concentrated to dry it under vacuum. A proper amount of the concentrate was dissolved in a 40% ethanol solution and analyzed by high performance liquid chromatography; as a result, the yield of each momilactone was as shown in Table 6. The yields of momilactones A and B produced according to the conventional method (method comprising inoculating rice blast fungus directly) are about 0.245 µg/ml and 0.864 µg/ml respectively, and hence it is clear that the yields of momilactons according to the present invention are extremely high as compared with those according to the conventional method.

TABLE 6

| Kind of momilactone | Yield of momilactone ug/culture supernatant 1 ml |
|---|---|
| Momilactone A | 3.3 |
| Momilactone B | 10.5 |

Figure 21:
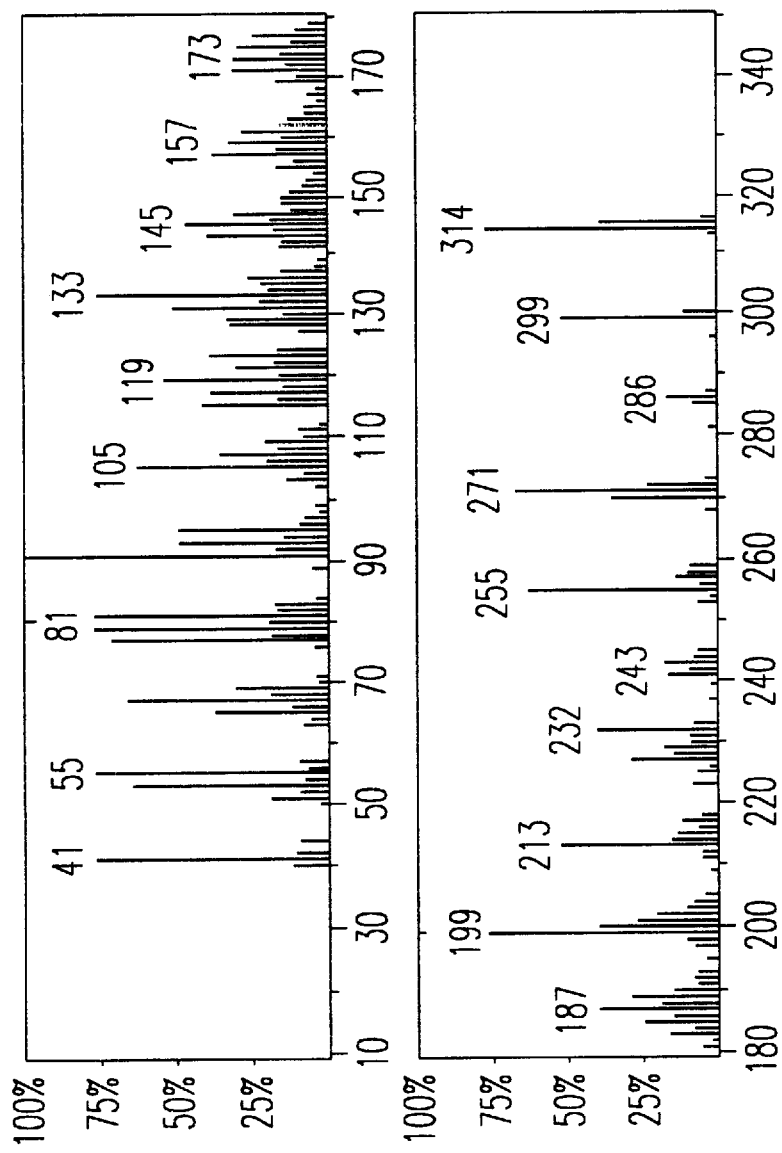
FIG. 21 shows a mass spectrum of momilactone A according to the present invention.
Figure 22:
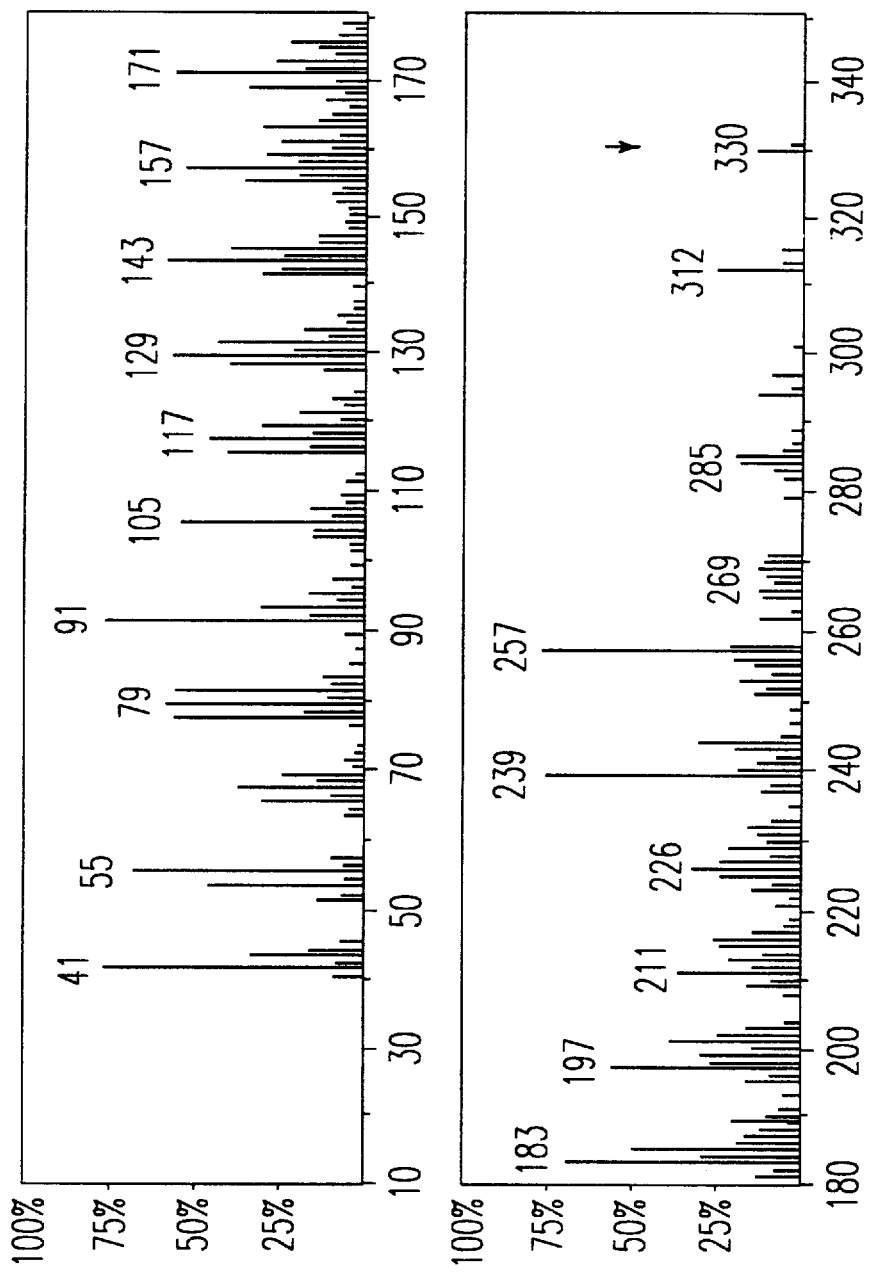
FIG. 22 shows a mass spectrum of momilactone B according to the present invention.
Figure 23:
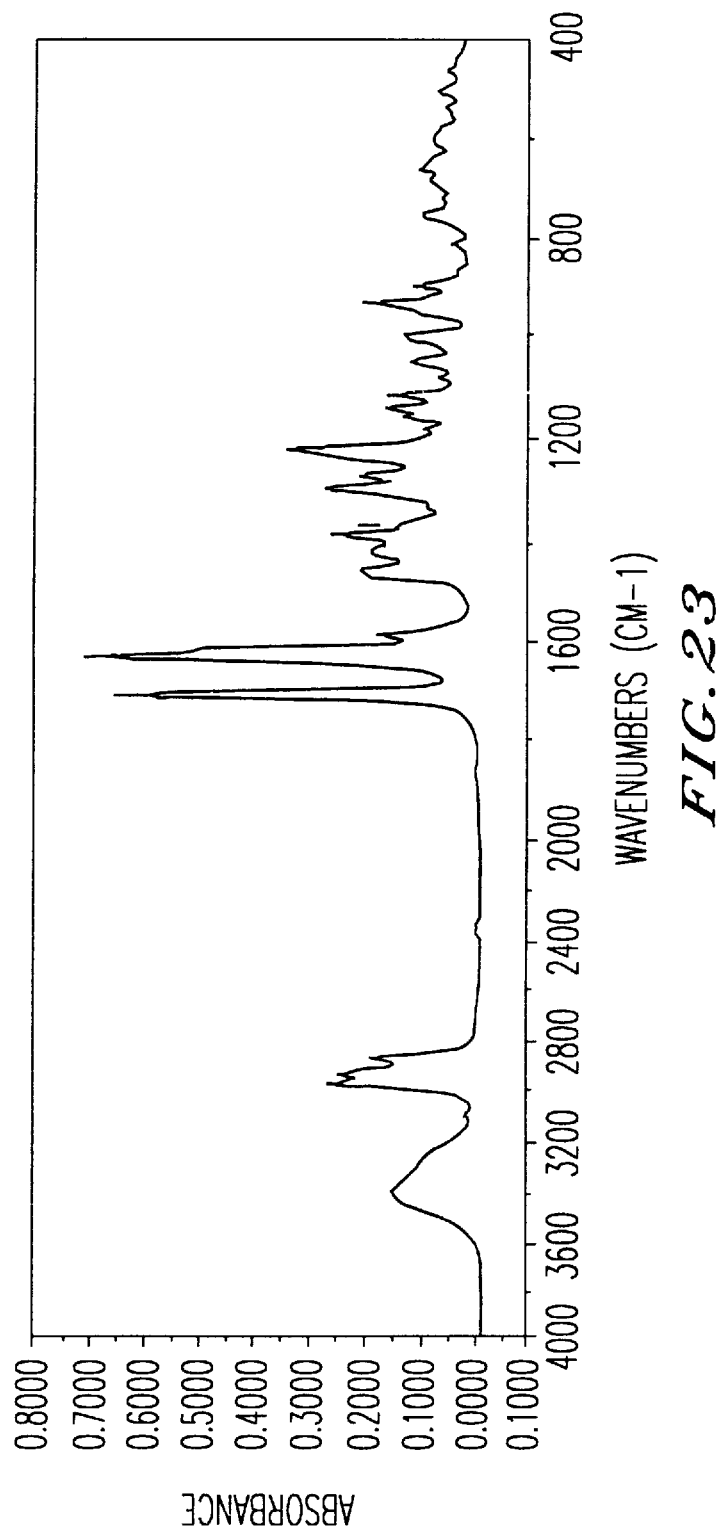
FIG. 23 shows an infrared absorption spectrum of phytocassane EL according to the present invention.
Figure 24:
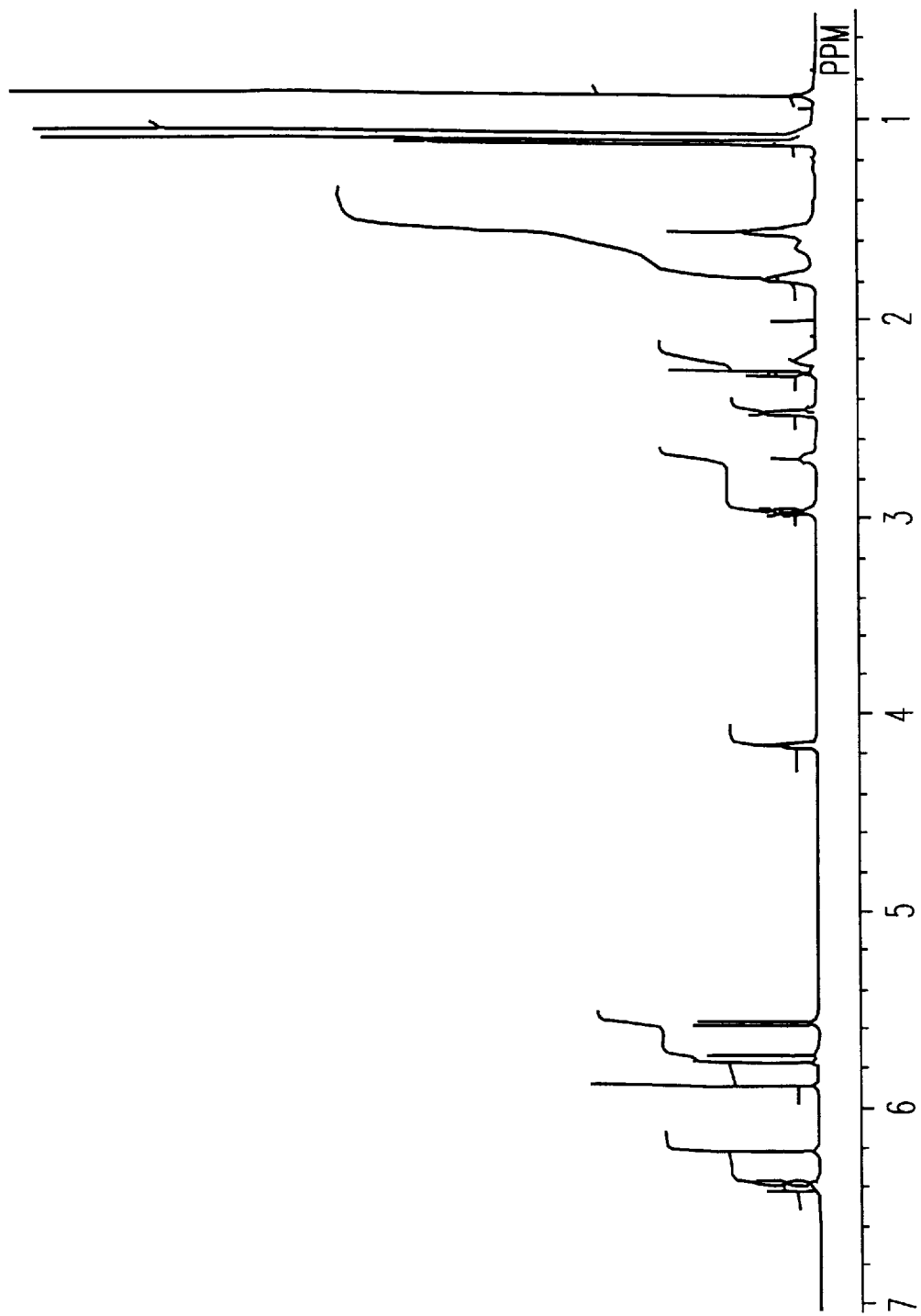
FIG. 24 shows an $^1$H-NMR spectrum of phytocassane EL according to the present invention.
Figure 25:
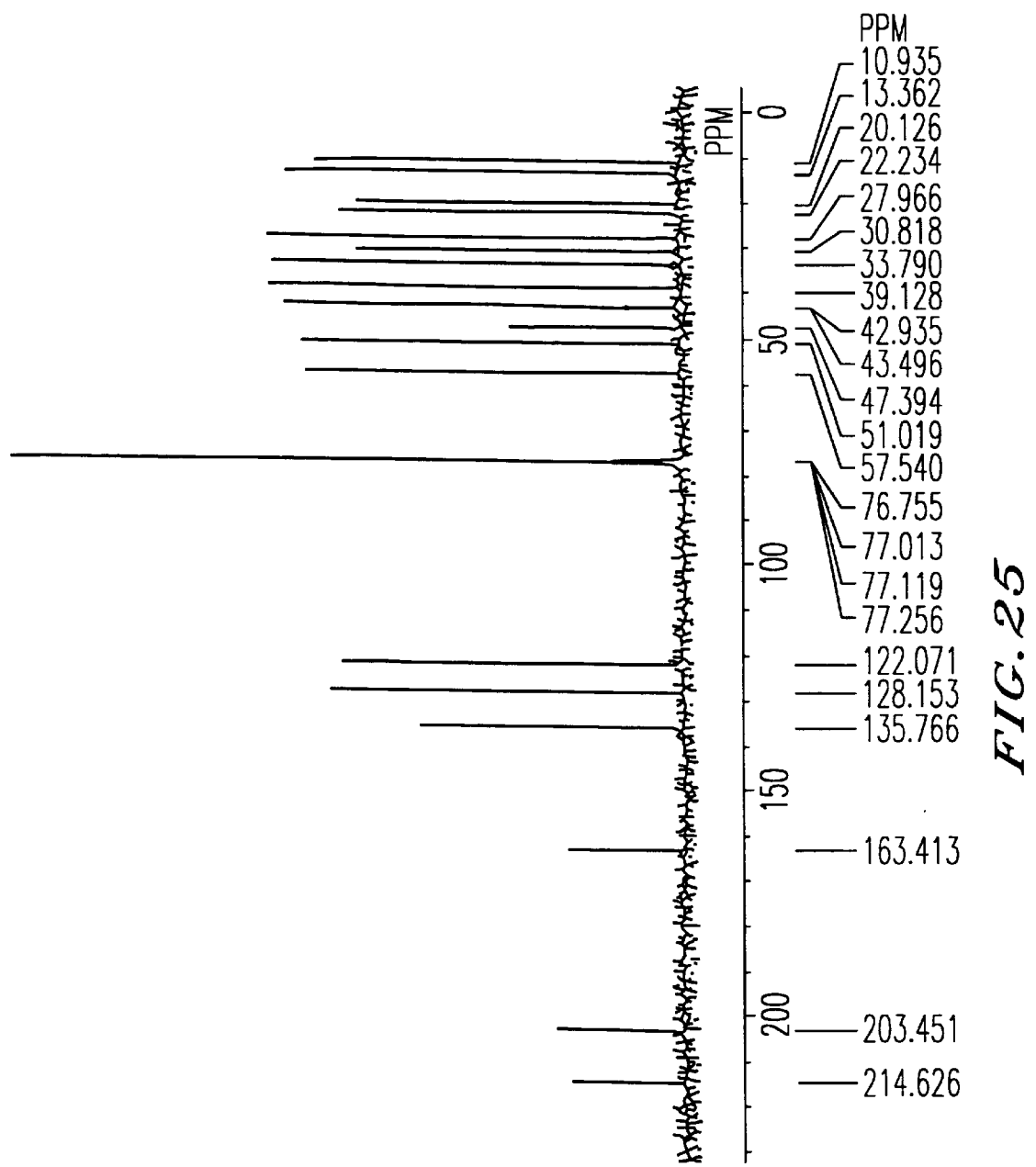
FIG. 25 shows a $^{13}$C-NMR spectrum of phytocassane EL according to the present invention.
Figure 26:
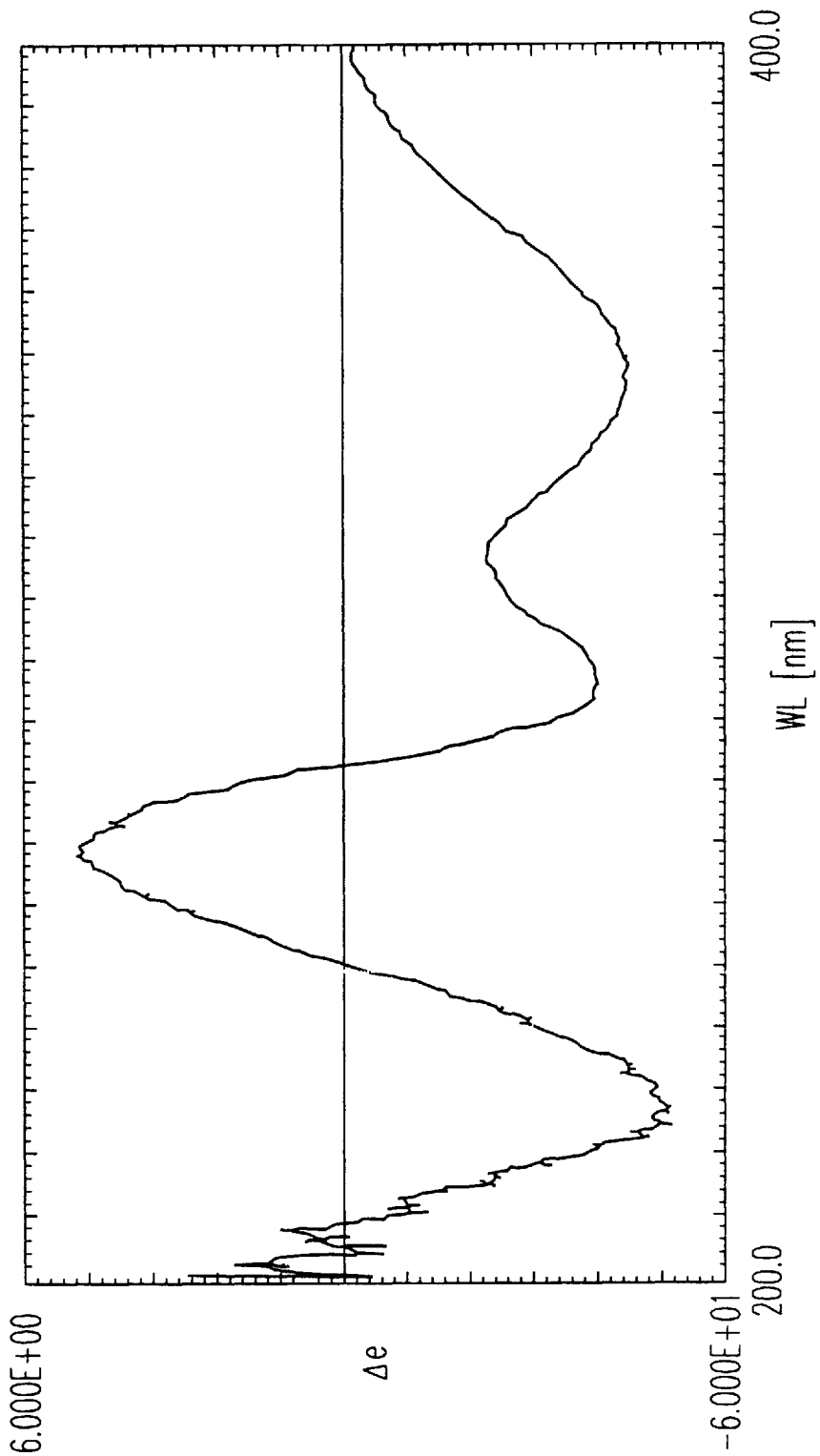
FIG. 26 shows a CD (circular dichroism) spectrum of phytocassane EL according to the present invention.

After each momilactone was fractioned by HPLC, the corresponding peak portion was collected and concentrated to dry it. The obtained product was dissolved in a small amount of acetone and analyzed by a gas chromatograph mass spectrometer; as a result, a mass spectrum showing the molecular ion peak corresponding to each molecular weight was obtained (FIGS. 21–22). As a result of performing analysis in the same manner employing cellular extract ingredients of Pyricularia oryzae, almost the same results were obtained.

EXAMPLE 6

(Production of phytocassane EL)

1) Proliferation of rice calluses

Rice (Koshihikari) calluses were subjected to rotary shaking culture (90 rpm, 25° C., 3,000 lux) in the DK medium (liquid medium containing the following; in 1 L, 30 g of sucrose, 0.809 g of $KNO_3$, 0.066 g of $(NH_4)SO_4$, 0.312 g of $NaH_2PO_4 \cdot 2H_2O$, 0.148 g of $CaCl_2 \cdot 2H_2O$, 0.246 g of $MgSO_4 \cdot 7H_2O$, 0.02 g of Fe-EDTA, 0.101 g of vitamins, 2 mg of glycine, 0.7 g of aspartic acid, 0.7 g of glutamine, 1 mg of 2,4-D, and other salts of $MnSO_4 \cdot 4\text{–}6H_2O$, $ZnSO_4 \cdot 7H_2O$, $CuSO_4 \cdot 5H_2O$, $Na_2MoO_4 \cdot 2H_2O$ and $H_3BO_4$ in required amounts) under the conditions of a pH of 5.8 and 25° C. A proper amount of calluses were sampled and crushed finely by a spatula, and only calluses passing through a 20-mesh sieve were selected.

2) Production of phytocassane EL

The sieved calluses were put into a 500-milliliter Erlenmeyer flask and 90 ml of the DK medium were added thereto and subjected to rotary shaking culture (90 rpm, 25° C., 3,000 lux) for two days; subsequently, 1 ml of a cellular extract ingredient solution of potato pathogenic fungi filtrated in aseptic condition was added into the culture broth, and the resultant culture broth was further subjected to rotary shaking culture for 4 days. After the completion of the culture, the culture broth was subjected to centrifugal separation (11,500 rpm, 2 hours) to separate a supernatant liquid.

3) Extraction and purification of phytocassane EL

Sodium carbonate was added to the supernatant to adjust a pH to 10.7, and then the same amount of ethyl acetate was added into the obtained supernatant to extract phytocassane EL and the extract was concentrated to dry it. Resultant residues were dissolved in ethanol to obtain a sample solution, which was subjected to separation and purification according to two-step high performance liquid chromatography (HPLC). That is, as a first step, the sample solution was introduced into a TSKgel ODS-120A column (21.5 mm×375 mm, manufactured by Toso) and eluted (10 ml/minute) with 55% acetonitrile. Phytocassane EL fractions with a retention time of about 41 minutes were collected and concentrated to dry it, and resultant residues were dissolved in ethanol. Next, as a second step, the sample solution was introduced into a TSKgel ODS-120T column (21.5 mm×375 mm, manufactured by Toso) and eluted (10 ml/minute) with 50% acetonitrile. Phytocassane EL fractions with a retention time of about 46 minutes were collected and concentrated to obtain a single phytocasane EL. About 3 mg of phytocassane EL were obtained from 1 L of the culture supernatant.

EXAMPLE 7
(Derivation of phytoalexins by phytocassane EL)
1) Production of phytoalexins
Phytocassane EL obtained in Example 1 was dissolved in a phosphoric acid buffer solution (20 mM, pH: 5.5) containing 0.1% of Tween 20 (manufactured by Wako Junyaku) to prepare sample solutions of 10 ppm and 20 ppm respectively. The sample solutions and a solvent liquid containing no sample were applied onto rice plants (Koshihikari) cultivated in pots to measure the derivative activity of producing phytoalexins. In this case, the application site was the tip part of the sixth leaf completely developed, and 20 μl (per leaf) of each sample solution were dropped on the ten points at proper spaces with a capillary pipette.
2) Extraction of phytoalexins
Rice plants treated with the sample solutions were cultured in an artificial weather room for 7 days, and then eight leaves were taken therefrom and cut into pieces; 5 ml of ethyl acetate and 5 ml of 0.1N sodium carbonate (pH: 10) were added therein and the mixture was shaken overnight. The ethyl acetate layer was collected and concentrated to dry it, and residues were dissolved in 0.4 ml of ethanol.
3) Analysis by HPLC
Into the solution were added 0.6 ml of 0.02N hydrochloric acid and mixed; the mixture was subjected to centrifugal separation, and 100 μl of the obtained supernatant liquid were subjected to analysis by high performance liquid chromatography (HPLC). The conditions of HPLC are as below:
Column: TSKgel ODS-120T (4.6 mm×300 mm, manufactured by Toso)
Solvent: Acetonitrile (45) : Water (55) (volume ratio)
Flow rate: 1.2 ml/min
Temperature: 50° C.
Detector: UV 280 nm (phytocassanes), 215 nm (momilactons)
In Table 7 below are shown the amounts of derived phytoalexins. As is apparent from the results shown in Table 7, phytocassane EL according to the present invention has a high activity of deriving phytoalexins (phytocassanes A, B, C and D, phytocassane EL, momilactones A and B) in rice plants at high yields.

EXAMPLE 8
(Test for inhibitory effects on hypha extension of rice blast fungus)
1) Process
A suspension was prepared by suspending spores of rice blast fungus (Pyricularia oryzae race 007) into water containing 100 ppm of Tween 20, and 25 μl thereof were put on a hole object glass plate. The plate was cultured at 28° C. for 6 hours to germinate. Separately, phytocassane EL samples were dissolved in water containing 500 ppm of Tween 20 in prescribed concentrations. To the suspensions of the germinated spores on the plate were added 25 μl of the aqueous phytocassane solutions with prescribed concentrations to prepare sample sections, and to the suspension was added 25 μl of water containing 500 ppm of Tween 20 to prepare a control section; each section was cultured at 28° C. overnight, and the state of the hyphae extension of each section was observed with a microscope.
2) Results
As a result, it was revealed that in the sample sections containing phytocassane EL, the extension of hyphae of rice blast fungus is inhibited and that phytocassane EL has an action of inhibiting the extension of hyphae of rice blast fungus. The concentration of phytocassane EL showing a length of a hypha of about 50% of that of the control section was 7 ppm.

EXAMPLE 9
(Test for inhibitory effects on hypha extension of rice sheath blight fungus)
1) Process
A commercially available potato dextrose agar medium (3.9 g) (manufactured by Eiken Kagaku) was dissolved in 100 ml, and 2 ml of the agar medium solution were poured into each test tube, sterilized by an autoclave at 121° C. for 15 minutes and cooled to 60° C. Separately, phytocassane EL samples were dissolved in water containing 500 ppm of Tween 20 in prescribed concentrations and subjected to filtration in aseptic condition. The phytocassane EL solutions were added into the agar medium solutions, mixed homogeneously and introduced into chalets to prepare agar plates containing 100 ppm of phytocassane EL. As a control, a blank plate was prepared by adding a corresponding amount of an aqueous Tween 20 solution of 500 ppm containing no phytocassane EL to the agar medium. A fragment of the rice sheath blight fungus (Rhizoctonia solani) cultured agar medium was put on the center of each chalet plate and cultured at 28° C., and the extension of hyphae after 40 hours was observed. Hyphae of each sample extended centering around the central inoculated points on the plate to form fungal mass.
2) Results
As a result, it was revealed that in the sample sections containing phytocassane EL, the extension of hyphae of rice

TABLE 7

| Phytocassane EL | Amount of Derived phytoalexins (μg/g leaves) | | | | | | |
|---|---|---|---|---|---|---|---|
| concentration (μg/ml) | Phytocassane A | Phytocassane B | Phytocassane C | Phytocassane D | Phytocassane EL | Momilactone A | Momilactone B |
| 0 | 1.3 | 1.5 | 0.3 | 0.1 | 0.2 | 6.2 | 0.8 |
| 20 | 11.4 | 15.6 | 8.6 | 2.2 | 5.4 | 33.4 | 5.1 |
| 40 | 21.3 | 12.5 | 10.1 | 4.1 | 12.7 | 42.1 | 6.9 | sheath blight fungus is inhibited and that phytocassane EL has an action of inhibiting the extension of hyphae of rice sheath blight fungus. While the diameter of fungal mass in the control plate was 18 mm, no extension of hyphae was observed in phytocassane EL of the 10 ppm section.

EXAMPLE 10

(Test for protecting effects on infection of rice blast fungus)

1) Process

Rice (Koshihikari) seeds were sowed in pots filled with culture soil at the rate of 8 seeds per pot, and were cultivated till the period developing 6 leaves, and two sections were subjected to a test, making 18 pots one section. Phytocassane EL was dissolved into a phosphoric acid buffer solution (20 mM, pH: 5.5) containing 0.1% of Tween 10 (manufactured by Wako Junyaku) in a concentration of 35 ppm to prepare a sample solution. Onto each section of rice plants were sprayed 50 ml of the phosphoric acid buffer solution containing 0.1% of Tween 20 and 50 ml of the sample solution, and they were left to stand at about 23° C. for 24 hours to dry the surface of leaves. Onto the surface of leaves in each section were sprayed 50 ml of a spore suspension of Pyricularia oryzae race 007 (strain having affinity), and the leaves were left to stand under the conditions of moistening and darkness for 24 hours to perform an inoculation treatment. Then, they were transferred into an artificial weather room to cultivate, and 5 days later, the number of grey spots of rice blast disease observed on each section of rice leaves was counted (average spot number of the disease per rice strain in 144 strains in 18 pots), and degrees of the outbreak of blast were compared.

2) Results

As a result, while the average spot number of the disease per rice strain was 2.17 in the section treated with the phosphoric acid buffer solution containing 0.1% of Tween 20, it was 0.91 in the section treated with the phytocassane EL sample solution; thus, the rice blast inhibitory effect of phytocassane EL was recognized clearly.

EXAMPLE 11

(Plant protection agent for control of rice blast)

Phytocassane EL and other ingredients were compounded at the following compounding rate and a liquid agent was prepared according to an ordinary procedure.

Phytocassane EL 35 μg/ml

Tween 20 (manufactured by Wako Junyaku) 500 ppm

Potassium phosphate buffer solution (20 mM, pH: 5.5) 100 ml

EXAMPLE 12

(Plant protection agent for control of rice sheath blight)

Phytocassane EL and other ingredients were compounded at the following compounding rate and a liquid agent was prepared according to an ordinary procedure.

Phytocassane EL 35 μg/ml

Tween 20 (manufactured by Wako Junyaku) 500 ppm

Potassium phosphate buffer solution (20 mM, pH: 5.5) 100 ml

Possibility for Industrial Utilization

The present invention relates to phytocassanes A, B, C and D, which are phytoalexins from rice and are novel dipertene compounds having an antifungal activity against rice blast fungus, Pyricularia oryzae and rice sheath blight, Rhizoctonia solani; according to the present invention, the following effects can be obtained.

(1) Novel dipertene compounds having a strong antifungal activity against Pyricularia oryzae and Rhizoctonia solani are provided.

(2) Since phytocassanes A, B, C and D have a strong antifungal activity against Pyricularia oryzae and Rhizoctonia solani, said compounds are useful as active ingredients for Pyricularia oryzae control drugs and Rhizoctonia solani control drugs.

(3) Low-toxic and harmless control drugs free from a so-called residual problem can be provided.

In addition, since a process for producing antifungal terpene compounds according to the present invention employs a liquid medium, tank culture can be performed and thereby a large amount of a sample can be prepared. Moreover, since a supernatant of a callus culture broth is employed as an extract material in this invention, a process of pulverization for rice plants is not needed and therefore admixture of pigments is small, and thereby procedures for extraction and purification become easy and a large amount of the sample can be prepared easily.

Moreover, by employing a solution of cellular extracts of plant pathogenic fungi such as Pyricularia oryzae and potato pathogenic fungi as a derivative substance, the yields of antifungal terpene compounds can be improved remarkably.

Further, phytocassane EL according to the present invention has an elicitor activity of deriving the formation of phytoalexins in rice plants and an antifungal activity against Pyricularia oryzae and Rhizoctonia solani, and the following effects can be obtained.

(1) Novel dipertene compounds deriving the formation of phytoalexins in rice plants and having an antifungal activity against Pyricularia oryzae and Rhizoctonia solani are provided.

(2) A process for producing phytocassane EL efficiently is provided.

(3) Since phytocassane EL derives the formation of phytoalexins in rice plants and has an antifungal activity against Pyricularia oryzae and Rhizoctonia solani, said compound is useful as an active ingredient for the protection agent for control of the rice diseases.

(4) Low-toxic and harmless protection agent for control of the rice disease free from a so-called residual toxicity problem can be provided.

What is claimed is:

1. Compound that is phytoalexins from rice, having antifungal activity against rice blast fungus, Pyricularia oryzae and rice sheath blight fungus, Rhizoctonia solani, and having a cassane skeleton represented by the following general formula (I):

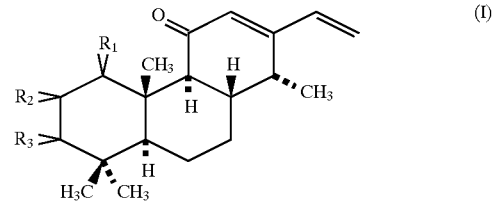

(wherein $R_1$ represents H and H or alpha-H and beta-OH; $R_2$ represents alpha-H and beta-OH, H and H or O; and $R_3$ represents O or alpha-H and beta-OH).

2. A process for producing an antifungal terpene compound as claimed in claim 1, comprising adding cellular extracts of plant pathogenic fungi to a liquid culture medium of rice calluses to produce the antifungal terpene compound, and then separating it.

3. Phytocassane EL having an activity of deriving the formation of phytoalexins in rice plants and antifungal activity against blast, fungi, Pyricularia oryzae, sheath blight fungus, *Rhizoctonia solani* represented by the following structural formula (II):

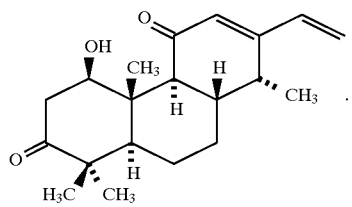
(II)

4. A process for producing phytocassane EL as claimed in claim 3, comprising adding cellular extracts of plant pathogenic fungi to a liquid culture medium of rice calluses to produce phytocassane EL, and then separating it.

5. A plant protection agent for control of rice blast disease containing phytocassane EL as claimed in claim 3 as an active ingredient.

6. A plant protection agent for control of rice sheath blight disease containing phytocassane EL as claimed in claim 3 as an active ingredient.

7. A process for production as claimed in claim 2, wherein the cellulose extracts of plant pathogenic fungi are rice blast fungi or potato pathogenic fungi.

8. A process for production as claimed in claim 3, wherein the cellulose extracts of plant pathogenic fungi are rice blast fungi or potato pathogenic fungi.

9. A process for production as claimed in claim 2, wherein the antifungal terpene compound is phytocassane A, B, C or D of formula (I) wherein

|  | R1 | R2 | R3 |
|---|---|---|---|
| Phytocassane A | H, H | α-H, β-OH | O |
| Phytocassane B | α-H, β-OH | α-H, β-OH | α-H, β-OH |
| Phytocassane C | α-H, β-OH | H, H | α-H, β-OH |
| Phytocassane D | H, H | O | α-H, β-OH |

10. A process for production as claimed in claim 2, wherein the antifungal terpene compound is momilactone A or B of the formula

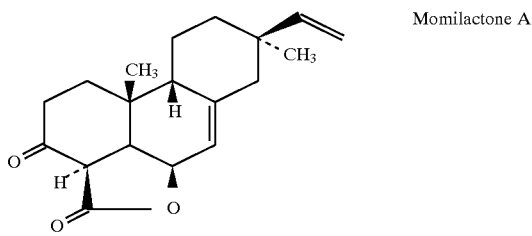

Momilactone A

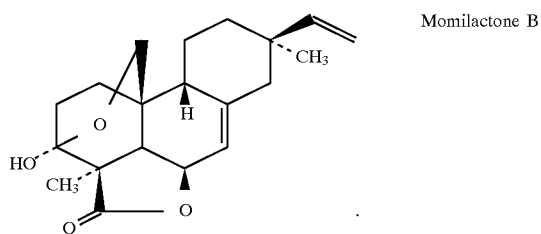

Momilactone B

* * * * *